(12) United States Patent
Desai et al.

(10) Patent No.: US 7,011,630 B2
(45) Date of Patent: Mar. 14, 2006

(54) METHODS FOR COMPUTING ROLLING ANALYTE MEASUREMENT VALUES, MICROPROCESSORS COMPRISING PROGRAMMING TO CONTROL PERFORMANCE OF THE METHODS, AND ANALYTE MONITORING DEVICES EMPLOYING THE METHODS

(75) Inventors: Shashi P. Desai, San Jose, CA (US); Timothy C. Dunn, San Francisco, CA (US); Matthew J. Lesho, San Carlos, CA (US); Russell O. Potts, San Francisco, CA (US); Janet A. Tamada, Stanford, CA (US); Charles W. Wei, Fremont, CA (US)

(73) Assignee: Animas Technologies, LLC, West Chester, PA (US)

( * ) Notice: Subject to any disclaimer, the term of this patent is extended or adjusted under 35 U.S.C. 154(b) by 318 days.

(21) Appl. No.: 10/176,965

(22) Filed: Jun. 21, 2002

(65) Prior Publication Data

US 2003/0050546 A1    Mar. 13, 2003

Related U.S. Application Data

(60) Provisional application No. 60/342,297, filed on Dec. 20, 2001, provisional application No. 60/300,511, filed on Jun. 22, 2001.

(51) Int. Cl.
  *A61B 5/00*    (2006.01)
(52) U.S. Cl. .................. 600/309; 600/365; 204/403.01; 204/406
(58) Field of Classification Search ................ 600/300, 600/301, 311–328, 345–381, 526, 529–532; 204/400, 403.01–403.1; 435/4–7.2; 436/43–54, 436/62–71; 438/43–54, 62–71
See application file for complete search history.

(56) References Cited

U.S. PATENT DOCUMENTS 4,724,845 A * 2/1988 Callahan ...................... 600/531

(Continued)

FOREIGN PATENT DOCUMENTS

WO      WO 96/00109        1/1996

(Continued)

OTHER PUBLICATIONS

Kurnik, et al., "Application of the Mixtures of Experts algorithm for signal processing in a noninvasive glucose monitoring system", *Sensors and Actuators B, Elsevier* 60, No. 1: 19-26 (1999).

(Continued)

*Primary Examiner*—Max F. Hindenburg
*Assistant Examiner*—Patricia Mallari
(74) *Attorney, Agent, or Firm*—RatnerPrestia

(57) ABSTRACT

The present invention relates to methods to increase the number of analyte-related signals used to provide analyte measurement values, e.g., when two or more analyte-related signals are used to obtain a single analyte measurement value a "rolling" value based on the two or more signals can be employed. In another aspect, interpolation and/or extrapolation methods are used to estimate unusable, missing or error-associated analyte-related signals. Further, interpolation and extrapolation of values are employed in another aspect of the invention that reduces the incident of failed calibrations. Further, the invention relates to methods, which employ gradients and/or predictive algorithms, to provide an alert related to analyte values exceeding predetermined thresholds. The invention includes the above-described methods, one or more microprocessors programmed to execute the methods, one or more microprocessors programmed to execute the methods and control at least one sensing and/or sampling device, and monitoring systems employing the methods described herein.

43 Claims, 6 Drawing Sheets

U.S. PATENT DOCUMENTS

| | | | |
|---|---|---|---|
| 5,226,417 A * | 7/1993 | Swedlow et al. | 600/336 |
| 5,279,543 A | 1/1994 | Glikfeld et al. | |
| 5,311,873 A * | 5/1994 | Savard et al. | 600/508 |
| 5,362,307 A | 11/1994 | Guy et al. | |
| 5,682,896 A * | 11/1997 | Scheib et al. | 600/456 |
| 5,695,623 A | 12/1997 | Michel et al. | |
| 5,713,353 A | 2/1998 | Castano | |
| 5,730,714 A | 3/1998 | Guy et al. | |
| 5,735,273 A | 4/1998 | Kurnik et al. | |
| 5,771,890 A | 6/1998 | Tamada | |
| 5,791,344 A * | 8/1998 | Schulman et al. | 600/347 |
| 5,827,183 A | 10/1998 | Kurnik et al. | |
| 5,840,020 A | 11/1998 | Heinonen et al. | |
| 5,954,685 A | 9/1999 | Tierney | |
| 5,989,409 A | 11/1999 | Kurnik et al. | |
| 5,995,860 A | 11/1999 | Sun et al. | |
| 6,023,629 A | 2/2000 | Tamada | |
| 6,026,314 A | 2/2000 | Amerov et al. | |
| 6,044,285 A | 3/2000 | Chaiken et al. | |
| 6,113,537 A | 9/2000 | Castano | |
| 6,139,718 A | 10/2000 | Kurnik et al. | |
| 6,141,573 A | 10/2000 | Kurnik et al. | |
| 6,144,869 A | 11/2000 | Berner et al. | |
| 6,174,289 B1 * | 1/2001 | Binder | 600/532 |
| 6,180,416 B1 | 1/2001 | Kurnik et al. | |
| 6,188,648 B1 | 2/2001 | Olsen | |
| 6,201,979 B1 | 3/2001 | Kurnik et al. | |
| 6,233,471 B1 | 5/2001 | Tierney et al. | |
| 6,272,364 B1 | 8/2001 | Kurnik | |
| 6,284,126 B1 | 9/2001 | Kurnik et al. | |
| 6,298,254 B1 | 10/2001 | Tamada | |
| 6,299,578 B1 | 10/2001 | Kurnik et al. | |
| 6,309,351 B1 | 10/2001 | Kurnik et al. | |
| 6,326,160 B1 | 12/2001 | Dunn et al. | |
| 6,529,752 B1 * | 3/2003 | Krausman et al. | 600/323 |
| 6,546,269 B1 | 4/2003 | Kurnik | |
| 6,595,919 B1 | 7/2003 | Berner et al. | |
| 6,633,772 B1 | 10/2003 | Ford et al. | |
| 6,653,091 B1 | 11/2003 | Dunn et al. | |

FOREIGN PATENT DOCUMENTS

| | | |
|---|---|---|
| WO | WO 99/58973 | 11/1999 |
| WO | WO 00/49941 | 8/2000 |
| WO | WO 01/88534 | 11/2001 |
| WO | WO 02/15777 | 2/2002 |

OTHER PUBLICATIONS

Tamada, et al., Noninvasive Glucose Monitoring Comprehensive Clinical Results, *JAMA 282*, No. 19: 1839-1844 (1999).

The Diabetes Control and Complication Trial Research Group., "The Effect of Intensive Treatment of Diabetes on the Development and Progression of Long-Term Complications in Insulin-Dependent Diabetes mellitus," *N. Engl. J. Med.* 329:997-1036 (1993).

Ohikubo et al., "Intensive Insulin Therapy Prevents the Progression of Diabetic Microvascular Complications in Japanese Patients with Non-Insulin-Dependent Diabetes Mellitus: A Randomized Prospective 6-year Study," *Diabetes Res. Clin Pract.* 28:103-117 (1995).

Tamada et al., "Noninvasive Glucose Monitoring," *JAMA* 282: 1839-1844 (1999).

* cited by examiner

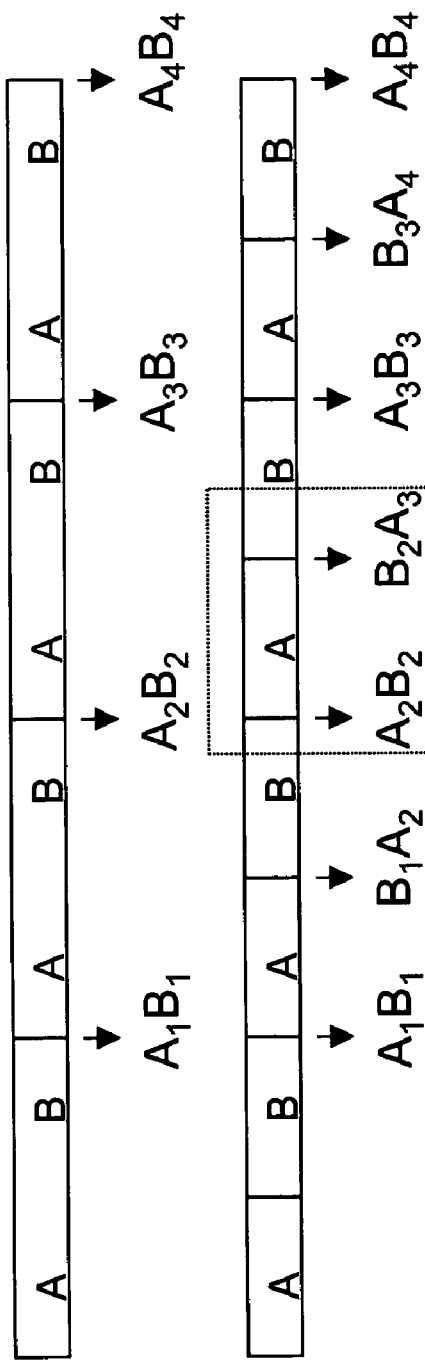
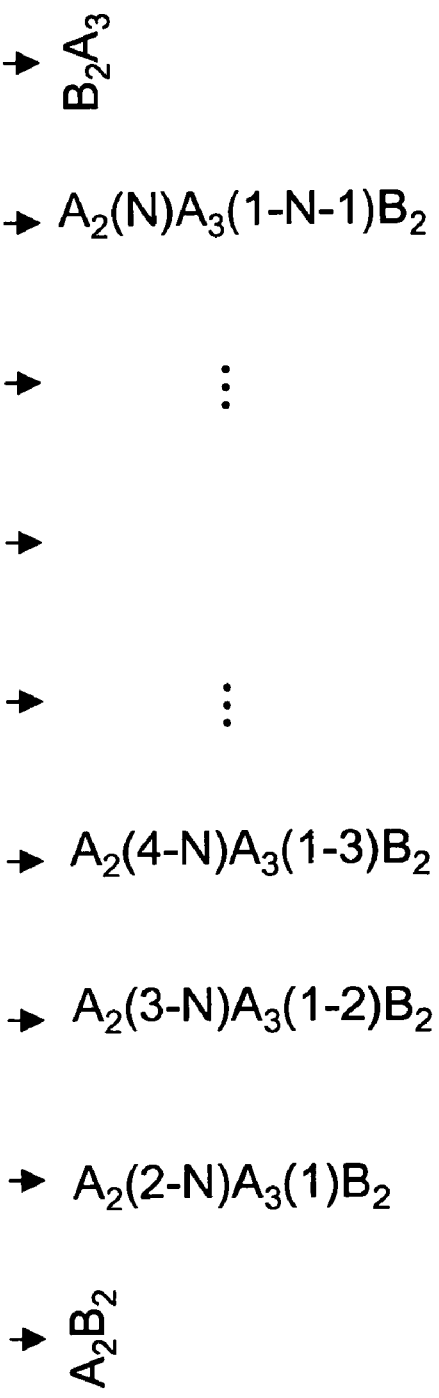
FIG. 3A
FIG. 3B
FIG. 3C

METHODS FOR COMPUTING ROLLING ANALYTE MEASUREMENT VALUES, MICROPROCESSORS COMPRISING PROGRAMMING TO CONTROL PERFORMANCE OF THE METHODS, AND ANALYTE MONITORING DEVICES EMPLOYING THE METHODS

CROSS-REFERENCE TO RELATED APPLICATION

This application is related to U.S. Provisional Patent Applications Ser. Nos. 60/300,511, filed 22, Jun. 2001, and 60/342,297, filed 20, Dec. 2001, from which priority is claimed under 35 USC §119(e)(1), and which applications are incorporated herein by reference in their entireties.

TECHNICAL FIELD

The present invention includes, but is not limited to, methods for improving the performance of an analyte monitoring system that provides a series of analyte-related signals over time, one or more microprocessors programmed to execute the methods, one or more microprocessors programmed to execute the methods and control a sensing device, one or more microprocessors programmed to execute the methods, control a sensing device, and control a sampling device, and monitoring systems employing the methods of the present invention. In one embodiment, the methods relate to glucose monitoring systems. In one aspect of the present invention, a rolling value is employed using signal data provided by an analyte sensor. The rolling value method of the present invention provides for more frequent updating and reporting of analyte measurement values. Another aspect of the present invention is employing interpolation and/or extrapolation methods to provide missing or error-associated signals in a series of analyte-related signals. Another aspect of the invention relates to methods of providing an alert related to analyte values exceeding predetermined thresholds (e.g., high and/or low thresholds) or ranges of values. In this aspect of the invention a gradient method and/or predictive algorithm method may be used. Yet another aspect of the present invention is a method for processing data from an analyte monitoring system that reduces the incidence of failed calibrations. The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

BACKGROUND OF THE INVENTION

Numerous systems for monitoring analyte (e.g., glucose) amount or concentration in a subject are known in the art, including, but not limited to the following: U.S. Pat. Nos. 5,362,307; 5,279,543; 5,695,623; 5,713,353; 5,730,714; 5,791,344; 5,840,020; 5,995,860; 6,026,314; 6,044,285; 6,113,537; 6,188,648, 6,326,160, 6,309,351, 6,299,578, 6,298,254, 6,284,126, 6,272,364, 6,233,471, 6,201,979, 6,180,416, 6,144,869, 6,141,573, 6,139,718, 6,023,629, 5,989,409, 5,954,685, 5,827,183, 5,771,890, and 5,735,273.

Self monitoring of blood glucose (BG) is a critical part of managing diabetes. However, most procedures for obtaining such information are invasive, painful and provide only periodic measurements. Results from the Diabetes Control and Complication Trial Research Group, (The Diabetes Control and Complication Trial Research Group. *N Engl J Med.* 1993;329:997–1036), UK Prospective Diabetes Study (UK Prospective Diabetes Study (UKPDS) Group. *Lancet.* 1998;352:837–853), and Kumamoto trials (Ohkubo Y, Kishikawa H, Araki E, et al. *Diabetes Res Clin Pract.* 1995;28: 103–117) showed that a tight glucose control regiment, which uses frequent glucose measurements to guide the administration of insulin or oral hypoglycemic agents, leads to a substantial decrease in the long-term complications of diabetes; however, there was a 3-fold increase in hypoglycemic events (The Diabetes Control and Complication Trial Research Group. *N Engl J Med.* 1993;329:997–1036.). Moreover, as many as 7 BG measurements per day were not sufficient to detect a number of severe hypoglycemic and hypoglycemic events (Ohkubo Y, Kishikawa H, Araki E, et al. *Diabetes Res Clin Pract.* 1995;28:103–117.).

The GlucoWatch® (Cygnus, Inc., Redwood City, Calif.) biographer provides a means to obtain painless, automatic, frequent and noninvasive glucose measurements (see, for example, U.S. Pat. Nos. 6,326,160, 6,309,351, 6,299,578, 6,298,254, 6,284,126, 6,272,364, 6,233,471, 6,201,979, 6,180,416, 6,144,869, 6,141,573, 6,139,718, 6,023,629, 5,989,409, 5,954,685, 5,827,183, 5,771,890, and 5,735,273). The device provides up to 3 readings per hour for as long as 12 hours after a single BG measurement for calibration (Tamada, et al., JAMA 282:1839–1844, 1999).

Such a monitoring system, which gives automatic and frequent measurement, supplies detailed information on glucose patterns and trends that might identify opportunities for improved BG control. Automatic readings also provide the opportunity for an alarm to be sounded in response to values below a user-selected alert level or as a result of rapid declines in the measured glucose values. Such alarms provide a method to reduce the risks of hypoglycemia and make intensive therapy for persons with diabetes safer and acceptable to more patients.

Further, such monitoring systems can be used to measure an amount or concentration, in a subject, of one or more analytes, where the one or more analytes may be in addition to or other than glucose (see, e.g., WO 96/00109, published 4, Jan. 1996.

The present invention offers methods of improving performance of analyte monitoring systems that supply a series of analyte-related signals over time, for example, the GlucoWatch biographer.

SUMMARY OF THE INVENTION

The present invention includes, but is not limited to, methods for improving the performance of an analyte monitoring system that provides a series of analyte-related signals over time, one or more microprocessors programmed to execute the methods, one or more microprocessors programmed to execute the methods and control a sensing device, one or more microprocessors programmed to execute the methods, control a sensing device, and control a sampling device, and monitoring systems employing the methods (comprising, for example, a sampling device, a sensing device, and one or more microprocessors programmed to control, for example, (i) a measurement cycle utilizing the sampling and sensing devices, and (ii) data gathering and data processing related to the methods of the present invention).

In a first aspect, the present invention relates to methods for calculating a series of average signals wherein (i) each average signal is calculated based on two or more contiguous (i.e., next to or near in time or sequence) signals in the series, and (ii) each average signal provides a measurement related to the amount or concentration of analyte in the subject; or, alternately calculating a series of sums, wherein (i) each summed signal is calculated based on two or more contiguous (i.e., next to or near in time or sequence) signals in the series, and (ii) each summed signal provides a measurement related to the amount or concentration of analyte in the subject. In this aspect the invention also comprises one or more microprocessors programmed to execute the methods, and monitoring systems employing the methods.

This aspect of the present invention is used, for example, in a method for monitoring an amount or concentration of analyte present in a subject, said method comprising:

providing a series of signals over time wherein each signal is related to the analyte amount or concentration in the subject; and calculating a series of average signals wherein (i) each average signal is calculated based on two or more contiguous (i.e., next to or near in time or sequence) signals in the series, and (ii) each average signal provides a measurement related to the amount or concentration of analyte in the subject; or calculating a series of sums, wherein (i) each summed signal is calculated based on two or more contiguous (i.e., next to or near in time or sequence) signals in the series, and (ii) each summed signal provides a measurement related to the amount or concentration of analyte in the subject. Missing signals in the series may be estimated using interpolation and/or extrapolation, and such estimated signals can be used in said calculations.

In this aspect, the present invention relates to methods of increasing the number of analyte measurement values related to the amount or concentration of an analyte in a subject as measured using an analyte monitoring device. In this method a series of analyte-related signals is obtained from the analyte monitoring device over time. Typically, two or more contiguous analyte-related signals are used to obtain a single analyte measurement value (M). In this method, paired analyte-related signals are typically used to calculate the measurement value. One improvement provided by the present method is that, prior to the present method, such an analyte monitoring device typically used paired signals to obtain a single measurement value; but an analyte-related signal from the monitoring device was not typically used to calculate more than one analyte measurement value. In the present method, the two or more contiguous analyte-related signals, used to obtain the single analyte measurement value, comprise first and last analyte-related signals of the series.

The method involves mathematically computing rolling analyte measurement values, wherein (i) each rolling analyte measurement value is calculated based on two or more contiguous analyte-related signals from the series of analyte-related signals obtained from the analyte monitoring device. Subsequent rolling analyte measurement values are mathematically computed by dropping the first analyte-related signal from the previous rolling analyte measurement value and including an analyte-related signal contiguous and subsequent to the last analyte-related signal used to calculate the previous rolling analyte measurement value. Further rolling analyte measurement values are obtained by repeating the dropping of the first analyte-related signal used to calculate the previous rolling analyte measurement and including an analyte-related signal contiguous and subsequent to the last analyte-related signal used to calculate the previous rolling analyte measurement. Each rolling analyte measurement value provides a measurement related to the amount or concentration of analyte in the subject. By employing this method the number of analyte measurement values, derived from the analyte-related signals in the series of analyte-related signals obtained from the analyte monitoring device, is increased by serially calculating rolling analyte measurement values.

In one embodiment of this aspect of the invention, the rolling analyte measurement value is, for example, an average of two or more analyte-related signals; alternately, the rolling analyte measurement value is a sum of two or more analyte-related signals. In another embodiment, each analyte-related signal is represented by an integral over time, and the rolling analyte measurement value is obtained by integral splitting.

The above method may be practiced, for example, using a monitoring device comprising a sampling device and a sensing device, wherein the series of analyte-related signals obtained from an analyte monitoring device is obtained as follows. Samples are extracted from the subject alternately into a first collection reservoir and then into a second collection reservoir using the sampling device, wherein (i) each sample comprises the analyte, and (ii) the sampling device comprises the first and second collection reservoirs. The analyte is sensed in each extracted sample to obtain a signal from each sample that is related to the analyte amount or concentration in the subject, thus providing a series of analyte-related signals. The sensing device may, for example, comprise first and second sensors, wherein the first sensor is in operative contact with the first collection reservoir and the sensing provides signal $S^A_j$ (where $S^A$ is the signal from sensor A, j is the time interval), the second sensor is in operative contact with the second collection reservoir and the sensing provides signal $S^B_{j+1}$ (where $S^B$ is the signal from sensor B, j+1 is the time interval), and an analyte measurement value is obtained using analyte-related signal from sensor A and sensor B. In this situation, the series of rolling analyte measurement values may be calculated employing the following equations:

$$(\text{average signal})_j = (S^B_{j-1} + S^A_j)/2, \qquad \text{Eqn. 1}$$

$$(\text{average signal})_{j+1} = (S^A_j + S^B_{j+1})/2; \qquad \text{Eqn. 2}$$

$$(\text{average signal})_{j+2} = (S^B_{j+1} + S^A_{j+2})/2; \text{ etc.}, \qquad \text{Eqn. 3}$$

wherein (i) (j−1) is the measurement half-cycle previous to j, and (j+2) is two measurement half-cycles after j, and (ii) each average signal corresponds to a rolling analyte measurement value.

Alternately, the series of rolling analyte measurement values may be calculated using the following equations:

$$(\text{summed signal})_j = (S^B_{j-1} + S^A_j); \qquad \text{Eqn. 4}$$

$$(\text{summed signal})_{j+1} = (S^A_j + S^B_{j+1}); \text{ and} \qquad \text{Eqn. 5}$$

$$(\text{summed signal})_{j+2} = (S^B_{j+1} + S^A_{j+2}); \text{ etc.} \qquad \text{Eqn. 6}$$

where (j−1) is the measurement half-cycle previous to j, and (j+2) is two measurement half-cycles after j; and (ii) each summed signal corresponds to a rolling analyte measurement value.

In one embodiment of this method, a missing or error-associated signal in the series of analyte-related signals obtained from the analyte monitoring device is estimated using interpolation before mathematically computing rolling analyte measurement values. Such missing or error-associated signals may also be estimated using extrapolation before mathematically computing rolling analyte measurement values.

In a preferred embodiment, the analyte is glucose. In one embodiment, the analyte monitoring device comprises (i) an iontophoretic sampling device, and (ii) an electrochemical sensing device. The analyte-related signal may, for example, be a current or a charge related to analyte amount or concentration of analyte in the subject.

One or more microprocessors may be utilized to mathematically compute rolling analyte measurement values employing the methods described herein. Further, such one or more microprocessors may be used to control operation of the components of the analyte-monitoring system (e.g., a sampling device and a sensing device of the monitoring system). In addition, the one or more microprocessors may control operation of other components, further algorithms, calculations, and/or the providing of alerts to a subject (user of the analyte-monitoring system). In this embodiment of the present invention one or more microprocessors may be utilized to execute the method as well as to control components of an analyte-monitoring system, for example, control obtaining samples and sensing analyte concentration in each obtained sample to provide a series of signals.

The present invention also includes analyte-monitoring devices employing the above methods.

In a second aspect the present invention comprises methods of interpolation and/or extrapolation to provide missing signals, where a series of signals is provided by an analyte monitoring system. Such an analyte monitoring system may comprise one or more sensors that provide the series of signals.

In one embodiment, the present invention includes the use of relationships between the signals obtained from different sensors to perform interpolation and/or extrapolation of estimated values. For example, in a two sensor system a ratio of signals obtained from a first sensor relative to a second sensor may be employed in such interpolations and/or extrapolations to estimate signal values.

One embodiment of this second aspect of the present invention includes a method of replacing unusable analyte-related signals when employing an analyte monitoring device to measure an analyte amount or concentration in a subject. A series of analyte-related signals, obtained from the analyte monitoring device over time, is provided wherein each analyte-related signal is related to the amount or concentration of analyte in the subject. An unusable analyte-related signal is replaced with an estimated signal, for example, by either:

(A) if one or more analyte-related signals previous to the unusable analyte-related signal and one or more analyte-related signals subsequent to the unusable analyte related signal are available, then interpolation is used to estimate the unusable, intervening analyte-related signal; or (B) if two or more analyte-related signals previous to the unusable analyte-related signal are available, then extrapolation is used to estimate the unusable, subsequent analyte-related signal.

In this method, the analyte monitoring device may comprise one or more sensor devices and a relationship between the signals obtained from the different sensor devices is used in interpolation and/or extrapolation calculation of estimated values. In one embodiment, the sensor device comprises two sensor elements and a ratio of signals obtained from a first sensor relative to a second sensor is employed in interpolation and/or extrapolation calculation of estimated signal values. For example, the analyte monitoring device may comprises a sampling device and a sensing device, wherein providing the series of analyte-related signals obtained from an analyte monitoring device comprises:

extracting a sample from the subject alternately into a first collection reservoir and then into a second collection reservoir using the sampling device, wherein (i) each sample comprises the analyte, and (ii) the sampling device comprises the first and second collection reservoirs; and sensing the analyte in each extracted sample to obtain a signal from each sample that is related to the analyte amount or concentration in the subject, thus providing a series of analyte-related signals, the sensing device comprising first and second sensors, wherein the first sensor is in operative contact with the first collection reservoir and the sensing provides signal $S^A_j$ (where $S^A$ is the signal from sensor A, j is the time interval), the second sensor is in operative contact with the second collection reservoir and the sensing provides signal $S^B_{j+1}$ (where $S^B$ is the signal from sensor B, j+1 is the time interval), and an analyte measurement value is obtained using analyte-related signal from sensor A and sensor B.

A relationship between the signals obtained from different sensors may be used in interpolation and/or extrapolation calculation of estimated values. For example, the relationship between the signals from the different sensors may take the form of a smoothed ratio:

$$R_i^s = wR_i + (1-W)R_{i-1}^s \qquad \text{Eqn. 10}$$

wherein, for example, $R_i$ is the A/B or B/A signal ratio for a $i^{th}$ measurement cycle, $R^S_i$ is smoothed R for a $i^{th}$ measurement cycle, and w is a smoothing factor and is represented by a fraction between and inclusive of 0 through 1, and $R^S_{i-1}$ is a smoothed ratio for the $(i-1)^{th}$ measurement cycle, wherein the $i^{th}$ measurement cycle is composed of first and second half-cycles and the second half-cycle value of the $i^{th}$ measurement cycle precedes $S_j$. In one embodiment, wherein a smoothed A/B ratio and a smoothed B/A ratio are employed, and the ratios are as follows:

$$\left(\frac{A}{B}\right)_{s,i} = w\left(\frac{A}{B}\right)_i + (1-w)\left(\frac{A}{B}\right)_{s,i-1} \qquad \text{Eqn. 9A}$$

$$\left(\frac{B}{A}\right)_{s,i} = w\left(\frac{B}{A}\right)_i + (1-w)\left(\frac{B}{A}\right)_{s,i-1} \qquad \text{Eqn. 9B}$$

wherein $(A/B)_{s,i}$ and $(B/A)_{s,i}$ refer to "smoothed" AB ratios for measurement cycle i, $(A/B)_i$ and $(B/A)_i$ refer to the AB ratio for measurement cycle i, and $(A/B)_{s,i-1}$ and $(B/A)_{s,i-1}$ refer to the smoothed AB ratio from the previous measurement cycle i−1.

For interpolation in the situation where both $S_j$ and $S_{j+2}$ are signals from the B sensor ($S^B_j$ and $S^B_{j+2}$), and $S_{j+1}$ is being estimated for the A sensor signal ($S^{AE}_{j+1}$), interpolation Eqn. 7A may be employed as follows:

$$S^{AE}_{j+1} = \frac{A}{B}\left\{S^B_j + (S^B_{j+2} - S^B_j)\frac{(t_{j+1} - t_j)}{(t_{j+2} - t_j)}\right\} \qquad \text{Eqn. 7A}$$

wherein $t_j$ is a measurement half-cycle, $t_{j+1}$, one subsequent half-cycle, and $t_{j+2}$ two subsequent half-cycles.

For interpolation in the situation where both $S_j$ and $S_{j+2}$ are signals from the A sensor ($S^A_j$ and $S^A_{j+2}$), and $S_{j+1}$ is being estimated for the B sensor signal ($S^{BE}_{j+1}$), interpolation Eqn. 7C may be employed as follows:

$$S^{BE}_{j+1} = \frac{B}{A}\left\{S^A_j + (S^A_{j+2} - S^A_j)\frac{(t_{j+1} - t_j)}{(t_{j+2} - t_j)}\right\}$$ Eqn. 7C wherein $t_j$, is a measurement half-cycle, $t_{j+1}$, one subsequent half-cycle, and $t_{j+2}$ two subsequent half-cycles.

For extrapolation in the situation where $S_j$ is signal from sensor A ($S^A_j$) and $S_{j+1}$ is signal from B sensor ($S^B_{j+1}$), and $S_{j+2}$ is being estimated for the A sensor signal ($S^{AE}_{j+2}$), extrapolation Eqn. 8A may be employed as follows:

$$S^{AE}_{j+2} = \frac{A}{B}(S^B_{j+1}) + \left[\left\{\frac{A}{B}(S^B_{j+1}) - S^A_j\right\}\frac{(t_{j+2} - t_{j+1})}{(t_{j+1} - t_j)}\right]$$ Eqn. 8A wherein $t_j$ is a measurement half-cycle, $t_{j+1}$, one subsequent half-cycle, and $t_{j+2}$ two subsequent half-cycles.

For extrapolation in the situation where $S_j$ is signal from the B sensor ($S^B_j$) and $S_{j+1}$ is signal from the A sensor ($S^A_{j+1}$), and $S_{j+2}$ is being estimated for the B sensor signal ($S^{BE}_{j+2}$), extrapolation Eqn. 8C may be employed as follows:

$$S^{BE}_{j+2} = \frac{B}{A}(S^A_{j+1}) + \left[\left\{\frac{B}{A}(S^A_{j+1}) - S^B_j\right\}\frac{(t_{j+2} - t_{j+1})}{(t_{j+1} - t_j)}\right]$$ Eqn. 8C wherein $t_j$ is a measurement half-cycle, $t_{j+1}$, one subsequent half-cycle, and $t_{j+2}$ two subsequent half-cycles.

In one embodiment the analyte is glucose. The analyte monitoring device may, for example, comprise (i) an iontophoretic sampling device, and (ii) an electrochemical sensing device. The analyte-related signal may be, e.g., a current or a charge related to analyte amount or concentration of analyte in the subject.

One or more microprocessors may be utilized to mathematically compute estimated signals employing the methods described herein. Further, such one or more microprocessors may be used to control operation of the components of the analyte monitoring system (e.g., a sampling device and a sensing device of the monitoring system). In addition, the one or more microprocessors may control operation of other components, further algorithms, calculations, and/or the providing of alerts to a subject (user of the analyte monitoring system).

The present invention also includes analyte monitoring devices employing the above methods.

In a third aspect, the present invention relates to a method for reducing the incidence of failed calibration for an analyte monitoring system that is used to monitor an amount or concentration of analyte present in a subject, where the monitoring system provides a series of signals or measurement values. For example, in one embodiment, the method comprises:

extracting a series of samples from the subject using a sampling device, said extracting alternately into a first collection reservoir and then into a second collection reservoir, wherein (1) each sample comprises the analyte, and (2) said sampling device comprises said first and second collection reservoirs;

sensing the analyte in each extracted sample to obtain a signal from each sample that is related to the analyte amount or concentration in the subject, thus providing a series of signals, said sensing device comprising a first sensor (A) and second sensor (B), wherein (1) said first sensor (A) is in operative contact with said first collection reservoir and said second sensor (B) is in operative contact with said second collection reservoir, (2) two consecutive signals comprise a measurement cycle, and each of the two consecutive signals is half-cycle signal; and performing a calibration method to relate analyte amount or concentration in the subject to signals obtained from the sensors, said calibration method comprising:

(i) obtaining a first half-cycle signal $S_j$, where a half-cycle signal $S_{j+1}$, or an estimate thereof, and a half-cycle signal $S_{j+2}$, or an estimate thereof, are both used in the calibration method so that the sensor signals correlate to the analyte amount or concentration in the subject, wherein the calibration method also employs an analyte calibration value that is independently determined;

(ii) providing the analyte calibration value;

(iii) selecting a conditional statement selected from the group consisting of:

(a) if neither the second half-cycle signal $S_{j+1}$ nor the third half-cycle signal $S_{j+2}$ comprise errors, then $S_{j+1}$ and $S_{j+2}$ are used in the calibration method;

(b) if only the second half-cycle signal $S_{j+1}$ comprises an error, then an estimated signal $S^E_{j+1}$ is obtained by determining an interpolated value using signal $S_j$ and $S_{j+2}$, wherein said interpolated value is $S^E_{j+1}$, and $S^E_{j+1}$ and $S_{j+2}$ are used in the calibration method;

(c) if only the third half-cycle signal $S_{j+2}$ comprises an error, then an estimated signal $S^E_{j+2}$ is obtained by determining an extrapolated value using signal $S_j$ and $S_{j+1}$, wherein said extrapolated value is $S^E_{j+2}$, and $S_{j+1}$ and $S^E_{1+2}$ are used in the calibration method; and (d) if both the second half-cycle signal $S_{j+1}$ and the third half-cycle signal $S_{j+2}$ comprise errors, then return to (i) to obtain a new half-cycle signal $S_j$ from a later measurement half-cycle than the first half-cycle signal, wherein said calibration method reduces the incidence of failed calibration for the analyte monitoring system.

In the above-described method for reducing the incidence of failed calibration, before performing said calibration method, a ratio of the signals obtained from the first sensor (A) and the second sensor (B) may be determined based on a series of signals obtained from first sensor (A) and second sensor (B), said ratio representing the relationship between sensor signals. One or more microprocessors may be programmed to provide the ratio.

The ratio of signals can be a smoothed ratio of the form:

$$R^s_i = wR_i + (1-w)R^s_{i-1}$$ Eqn. 10 wherein, $R_i$ is the A/B or B/A ratio for a $i^{th}$ measurement cycle, $R^S_i$ is smoothed R for a $i^{th}$ measurement cycle, and w is a smoothing factor and represents a numerical, percentage value between and inclusive of 0 through 100%, where w is represented by a fraction between and inclusive of 0 through 1, and $R^S_{i-1}$ is a smoothed ratio for the $(i-1)^{th}$ measurement cycle, wherein the $i^{th}$ measurement cycle is composed of first and second half-cycles and the second half-cycle value of the $i^{th}$ measurement cycle precedes $S_j$. A single $R^S_i$ may be used or more than one such ratio may be employed.

In one embodiment of the method for reducing the incidence of failed calibration in a two sensor system, two smoothed AB ratios may be employed:

$$\left(\frac{A}{B}\right)_{s,i} = w\left(\frac{A}{B}\right)_i + (1-w)\left(\frac{A}{B}\right)_{s,i-1} \quad \text{Eqn. 9A}$$

$$\left(\frac{B}{A}\right)_{s,i} = w\left(\frac{B}{A}\right)_i + (1-w)\left(\frac{B}{A}\right)_{s,i-1} \quad \text{Eqn. 9B}$$

In Eqn. 9A and Eqn. 9B, $(A/B)_{s,i}$ and $(B/A)_{s,i}$ refer to "smoothed" AB ratios for measurement cycle i, $(A/B)_i$ and $(B/A)_i$, refer to the AB ratio for measurement cycle i, and $(A/B)_{s,i-1}$ and $(B/A)_{s,i-1}$, refer to the smoothed AB ratio from the previous measurement cycle i-1. In the Holt-Winters smoothing presented above, the determination of the smoothed AB ratio depends on the adjustable parameter w (a weighting factor). In one embodiment of the present invention, w is 70% (0.70).

In one embodiment of the method for reducing the incidence of failed calibration in a two-sensor system (wherein two AB ratios are employed, conditional statement (b) is selected, and said interpolated value is determined by an interpolation calculation) Eqn. 7A through Eqn. 7D may be employed for interpolation in the following situations:

in the situation where both $S_j$ and $S_{j+2}$ are signals from the B sensor ($S^B_j$ and $S^B_{j+2}$), and $S_{j+1}$ is being estimated for the A sensor signal ($S^{AE}_{j+1}$), interpolation Eqn. 7A may be employed as follows:

$$S^{AE}_{j+1} = \frac{A}{B}\left\{S^B_j + (S^B_{j+2} - S^B_j)\frac{(t_{j+1} - t_j)}{(t_{j+2} - t_j)}\right\} \quad \text{Eqn. 7A}$$

wherein t is the time interval, for example, measurement half-cycle $t_j$, one subsequent half-cycle, $t_{j+1}$, or two subsequent half-cycles $t_{j+2}$. When the points are equally spaced, that is when $2(t_{j+1}-t_j)=(t_{j+2}-t_j)$, then Eqn. 7A reduces to the following Eqn. 7B:

$$S^{AE}_{j+1} = \frac{A}{B}\left(\frac{S^B_j + S^B_{j+2}}{2}\right) \quad \text{Eqn. 7B}$$

In the situation where both $S_j$ and $S_{j+2}$ are signals from the A sensor ($S^A_j$ and $S^A_{j+2}$), and $S_{j+1}$ is being estimated for the B sensor signal ($S^{BE}_{j+1}$), interpolation Eqn. 7C may be employed as follows:

$$S^{BE}_{j+1} = \frac{B}{A}\left\{S^A_j + (S^A_{j+2} - S^A_j)\frac{(t_{j+1} - t_j)}{(t_{j+2} - t_j)}\right\} \quad \text{Eqn. 7C}$$

When the points are equally spaced, that is when $2(t_{j+1}-t_j)=(t_{j+2}-t_j)$, then Eqn. 7C reduces to the following Eqn. 7D:

$$S^{BE}_{j+1} = \frac{B}{A}\left(\frac{S^A_j + S^A_{j+2}}{2}\right). \quad \text{Eqn. 7D}$$

In a further embodiment of the method for reducing the incidence of failed calibration in a two sensor system (wherein two AB ratios are employed, conditional statement (c) is selected, and said extrapolated value is determined by an extrapolation method) Equations 2A and 2B may be employed for extrapolation in the following situations:

in the situation where $S_j$ is signal from sensor A ($S^A_j$) and $S_{j+1}$ is signal from B sensor ($S^B_{j+1}$), and $S_{j+2}$ is being estimated for the A sensor signal ($S^{AE}_{j+2}$), extrapolation Eqn. 8A may be employed as follows:

$$S^{AE}_{j+2} = \frac{A}{B}(S^B_{j+1}) + \left[\left\{\frac{A}{B}(S^B_{j+1}) - S^A_j\right\}\frac{(t_{j+2} - t_{j+1})}{(t_{j+1} - t_j)}\right] \quad \text{Eqn. 8A}$$

When the points are equally spaced, that is when $(t_{j+2}-t_{j+1})=(t_{j+1}-t_j)$, then Eqn. 8A reduces to the following Eqn. 8B:

$$S^{AE}_{j+2} = 2\frac{A}{B}S^B_{j+1} - S^A_j \quad \text{Eqn. 8B}$$

In the situation where $S_j$ is signal from the B sensor ($S^B_j$) and $S_{j+1}$ is signal from the A sensor ($S^A_{j+1}$), and $S_{j+2}$ is being estimated for the B sensor signal ($S^{BE}_{j+2}$), extrapolation Eqn. 8C may be employed as follows:

$$S^{BE}_{j+2} = \frac{B}{A}(S^A_{j+1}) + \left[\left\{\frac{B}{A}(S^A_{j+1}) - S^B_j\right\}\frac{(t_{j+2} - t_{j+1})}{(t_{j+1} - t_j)}\right] \quad \text{Eqn. 8C}$$

When the points are equally spaced, that is when $(t_{j+2}-t_{j+1})=(t_{j+1}-t_j)$, then Eqn. 8C reduces to the following Eqn. 8D:

$$S^{BE}_{j+2} = 2\frac{B}{A}S^A_{j+1} - S^B_j. \quad \text{Eqn. 8D}$$

In these embodiments of the present invention one or more microprocessors may be utilized to execute the interpolation methods, extrapolation methods, and/or the method for reducing the incidence of failed calibration, as well as to control components of an analyte monitoring system, for example, control extracting samples, sensing analyte concentration in each obtained sample, and selecting conditional statements based on obtained criteria.

In this third aspect of the invention, the method may further comprise waiting for an un-skipped half-cycle signal ($S_j$) before initiating the calibration method.

In one embodiment of this third aspect of the present invention, the analyte is glucose. The analyte monitoring device may, for example, comprise (i) an iontophoretic sampling device, and (ii) an electrochemical sensing device. The analyte-related signal may be, e.g., a current or a charge related to analyte amount or concentration of analyte in the subject.

One or more microprocessors may be utilized to control operation of the calibration method employing the methods described herein. Further, such one or more microprocessors may be used to control operation of the components of the analyte monitoring system (e.g., a sampling device and a sensing device of the monitoring system). In addition, the one or more microprocessors may control operation of other components, further algorithms, calculations, and/or the providing of alerts to a subject (user of the analyte monitoring system).

The present invention also includes analyte monitoring devices employing the above methods.

In a fourth aspect, the present invention teaches a method comprising waiting for an unskipped (i.e., error free or good signal) half-cycle signal before initiating a calibration sequence (e.g., before opening a calibration window inviting the user to provide to a monitoring system an independently determined analyte calibration value).

In a fifth aspect, the present invention describes methods for predicting an analyte concentration-related event when an analyte level falls above or below predetermined thresholds or outside of a predetermined range of reference values, microprocessors programmed to execute these methods, and analyte monitoring systems employing these methods. The methods provide for predicting an analyte concentration-related event in a subject being monitored for levels of a selected analyte. The methods of the invention typically employ multiple parameters to be used in prediction of the hypoglycemic event. Such parameters include, but are not limited to, current glucose readings (reflecting glucose amount or concentration in the subject), one or more predicted future glucose reading, time intervals, trends, skin conductance, and skin temperature. In one aspect, the analyte being monitored is glucose and the present invention comprises a method for predicting a hypoglycemic and/or hyperglycemic event in a subject.

The method comprises determining threshold values (or ranges of values) for the selected parameters, wherein the threshold values (or ranges of values) are indicative of an analyte concentration-related event in the subject: e.g., determining a threshold glucose value (or range of values) that corresponds to a hypoglycemic event. A series of analyte measurement values is typically obtained at selected time intervals. In one embodiment the time intervals are evenly spaced. Such a series may be obtained, for example, using a method comprising: extracting a sample comprising the analyte, e.g., glucose, from the subject using a transdermal sampling system that is in operative contact with a skin or mucosal surface of the subject; obtaining a raw signal from the extracted analyte, wherein the raw signal is specifically related to analyte amount or concentration in the subject; correlating the raw signal with an analyte measurement value indicative of the amount or concentration of analyte present in the subject at the time of extraction; and repeating the extracting, obtaining, and correlating to provide a series of measurement values at selected time intervals. In one embodiment, the sampling system used to extract samples is maintained in operative contact with the skin or mucosal surface of the subject during the extracting, obtaining, and correlating to provide for frequent analyte measurements (e.g., glucose measurements).

In this aspect of the present invention, one or more gradient methods may be employed to examine the trend of analyte values, and/or one or more predictive algorithms may be employed to predict an analyte measurement value for a further time interval subsequent to the series of measurement values. In one embodiment of this aspect of the present invention, the series of measurement values comprises two or more discrete values.

Several models for the determination of a gradient (i.e., the rate of change) are as follows:

Model A: $\frac{y_{(n)} - y_{(n-1)}}{\Delta t}$ (concentration/time); where $\Delta t = (t_{(n)} - t_{(n-1)})$ Model B: $\frac{y_{(n)} - y_{(n-1)}}{y_{(n-1)} \Delta t}$ (fractional change/time); where $\Delta t = (t_{(n)} - t_{(n-1)})$ -continued Model C: $\frac{y_{(n)} - y_{(n-2)}}{\Delta t}$ (concentration/time); where $\Delta t = (t_{(n)} - t_{(n-2)})$ Model D: $\frac{y_{(n)} - y_{(n-2)}}{y_{(n-2)} \Delta t}$ (fractional change/time); where $\Delta t = (t_{(n)} - t_{(n-2)})$ Model E: Average $\left[ \frac{y_{(n)} - y_{(n-1)}}{\Delta t_1}, \frac{y_{(n-1)} - y_{(n-2)}}{\Delta t_2}, \frac{y_{(n)} - y_{(n-2)}}{\Delta t_3} \right]$ (concentration/time);

where $\Delta t_1 = (t_{(n)} - t_{(n-1)})$, $\Delta t_2 = (t_{(n-1)} - t_{(n-2)})$, and $\Delta t_3 = (t_{(n)} - t_{(n-2)})$. In this model, the average is of all three values shown in the brackets.

Model F: $\frac{y_{(n)} - y_{(n-3)}}{y_{(n-3)} \Delta t}$ (fractional change/time); where $\Delta t = (t_{(n)} - t_{(n-3)})$ In the above models, $y_n$ stands for an analyte reading at time point $t_{(n)}$, $y_{(n-1)}$ an analyte reading at time point $t_{(n-1)}$ (i.e., the previous reading to $y_n$), $y_{(n-2)}$ an analyte reading at time point $t_{(n-2)}$ (i.e., the reading previous to $y_{(n-1)}$), $y_{(n-3)}$ an analyte reading at time point $t_{(n-3)}$ (i.e., the reading previous to $y_{(n-2)}$). Each of the above methods give a rate of change. Models A, C, and E give concentration change per time interval (e.g., for glucose mg/dL/minute (milligrams of glucose per deciliter per minute) or mmol/L/minute), whereas Models B, D, and F gives fractional change per time interval (e.g., a percentage change in the glucose reading per minute). When using a gradient method a threshold of an acceptable rate of change is selected (for example, based on experimental data and/or acceptable ranges of measurement values).

The selected model calculates the rate of change (e.g., in the indicated units) and an algorithm compares the calculated rate of change to the acceptable rate of change. If the calculated rate of change surpasses the acceptable rate of change then a alert may be provided to the user. In one embodiment, a microprocessor employs an algorithm comprising the selected model and calculates the rate of change (e.g., in the indicated units). The microprocessor then employs an algorithm to compare the calculated rate of change to a predetermined acceptable rate of change. If the calculated rate of change differs significantly from the acceptable rate of change then the microprocessor triggers the analyte monitoring system to provide an alert to the user. Typically when employing the gradient models, to provide a low-analyte alert (e.g., hypoglycemic event alert) the calculated rate of change is negative and less than the predetermined threshold rate of change; and/or to provide a high-analyte alert (e.g., hyperglycemic event alert) the calculated rate of change is positive and greater than the predetermined threshold rate of change. Alternatively, absolute values of the calculated and threshold rates of change may be used for comparison. In this case, an alert is provided when the absolute value of the calculated rate of change is greater than the absolute value of predetermined threshold rate of change.

Exemplary predictive algorithm methods include, but are not limited to, the following:

$$y_{(n+1)} = y_{(n)} + \alpha(y_{(n)} - y_{(n-1)}) + \frac{\alpha^2}{2}(y_{(n)} - 2y_{(n-1)} + y_{(n-2)}) \quad \text{Eqn. 11}$$

$$y_{(n+1)} = y_{(n)} + \frac{(y_{(n)} - y_{(n-1)})}{(t_n - t_{(n-1)})} * (t_{(n+1)} - t_n) \quad \text{Eqn. 12}$$

$$y_{(n+1)} = \frac{5}{2}y_{(n)} + -2(y_{(n-1)}) + \frac{1}{2}(y_{(n-2)}) \quad \text{Eqn. 13}$$

$$y_{(n+2)} = y_{(n)} + \frac{(y_{(n)} - y_{(n-2)})}{(t_n - t_{(n-2)})} * (t_{(n+2)} - t_n) \quad \text{Eqn. 14}$$

$$y_{(n+2)} = y_{(n)} + \frac{(y_{(n)} - y_{(n-1)})}{(t_n - t_{(n-1)})} * (t_{(n+2)} - t_n) \quad \text{Eqn. 15}$$

In these equations, the methods calculate the predicted value of a variable y at time $t_{n+1}$ (or $t_{n+2}$, as indicated) as a function of that variable at the current time $t_n$, as well as at a previous time or times, e.g., $t_{n-1}$ and/or $t_{n-2}$). In Eqn. 11, α is an empirically determined weighting value that is typically a real number between 0 and 1. Each of the above methods provides a predicted analyte value, for example, an amount or concentration (e.g., the units may be mg/dL or mmol/L when y is a glucose reading). When using a predictive algorithm, thresholds of an acceptable range for analyte amount or concentration are selected (for example, based on experimental data and/or acceptable ranges of measurement values). High threshold values may be selected (e.g., a glucose value that is considered hyperglycemic for a subject), low threshold values may be selected (e.g., a glucose value that is considered hypoglycemic for a subject), and/or an acceptable range of values with an associated error may also be employed.

In one embodiment, one or more microprocessors employ an algorithm comprising the selected predictive algorithm and calculates the predicted value (e.g., in the indicated units). The microprocessor then employs an algorithm to compare the predicted value to the threshold value(s). If the predicted value falls above a high threshold, below a low threshold, or outside of a predetermined range of values, then the microprocessor triggers the analyte monitoring system to provide an alert to the user.

When the analyte being monitored is glucose and glucose readings are provided by a glucose monitoring device $y_n$ corresponds to $GW_n$, a glucose value in the subject at time $t_n$. Further, for prediction of glucose values when using Eqn. 11, α is typically in the range of 0.5–0.7.

In a further embodiment of this aspect of the present invention, an approach combining the above-described gradient method and predictive algorithm method is employed. In this embodiment of the present invention, rate of change thresholds are determined as well as analyte thresholds (or range of values). Generally, a predictive algorithm is chosen which provides a predicted analyte value at a future time point. The predicted value is compared to the threshold value for the alert. If the predicted value exceeds the threshold value, then the rate of change of the analyte is evaluated. If the rate of change of the analyte level also surpasses a predetermined threshold (or falls outside of a range of values) then an analyte concentration-related alert is provided to the subject in whom the analyte levels are being monitored. Of course the order of these two comparisons (i.e., predicted value and rate of change) may be reversed, for example, where the rate of change is evaluated first and then the predicted value is evaluated. In one embodiment of the present invention, a future analyte measurement value (e.g., a glucose measurement value) is predicted using Eqn. 11 and a gradient analysis is performed using Model B.

When employing the above gradient methods and/or predictive algorithms, an alert/alarm can be used to notify the subject (or user) if the predicted value is above/below a predetermined threshold.

In a further embodiment of the present invention, the rolling values described above are employed as the measurement data points in the analyte concentration-related alert methods. In yet a further aspect of the present invention interpolation and/or extrapolation methods are employed to provide missing or error-associated signals in the series of analyte-related signals.

One or more microprocessors may be utilized to control prediction of an analyte-concentration related event employing the methods described herein. Further, such one or more microprocessors may be used to control operation of the components of the analyte monitoring system (e.g., a sampling device and a sensing device of the monitoring system). In addition, the one or more microprocessors may control operation of other components, further algorithms, calculations, and/or the providing of alerts to a subject (user of the analyte monitoring system).

The present invention also includes analyte monitoring devices employing the above methods.

In one embodiment of this aspect of the present invention, the sample comprising glucose is extracted from the subject into a collection reservoir to obtain an amount or concentration of glucose in the reservoir. Such one or more collection reservoirs are typically in contact with the skin or mucosal surface of the subject and the sample is extracted using an iontophoretic current applied to the skin or mucosal surface. Further, at least one collection reservoir may comprise an enzyme that reacts with the extracted glucose to produce an electrochemically detectable signal, e.g., glucose oxidase. Alternatively, the series of glucose measurement values may be obtained with a different device, for example, using a near-infrared spectrometer.

This aspect of the present invention also comprises a glucose monitoring system useful for performing the methods of the present invention. In one embodiment, the glucose monitoring system comprises, in operative combination, a sensing mechanism (in operative contact with the subject or with a glucose-containing sample extracted from the subject, wherein the sensing mechanism obtains a raw signal specifically related to glucose amount or concentration in the subject), and one or more microprocessors in operative communication with the sensing mechanism. The microprocessors comprise programming to (i) control the sensing mechanism to obtain a series of raw signals at selected time intervals, (ii) correlate the raw signals with measurement values indicative of the amount or concentration of glucose present in the subject to obtain a series of measurement values, (iii) predict a measurement value at a further time interval, which occurs after the series of measurement values is obtained, (iv) compare the predicted measurement value to a predetermined threshold value or range of values, wherein a predicted measurement value lower than the predetermined threshold value is designated to be hypoglycemic, (v) calculate a gradient, (vi) compare the gradient value to a predetermined threshold value/trend or range of values/trends, wherein when the calculated rate of change is negative and less than the predetermined threshold rate of change this is indicative of a hypoglycemic event; and (vii) predict a hypoglycemic event in the subject when both (a) comparing the predicted measurement value to the threshold glucose value (or range of values) indicates a hypoglycemic event, and (b) comparing the gradient reading with a threshold parameter value, range of values, or trend of parameter values indicates a hypoglycemic event.

Embodiments of all of the above aspects of the present invention may include application of sampling techniques/devices including, but not limited to, the following: iontophoresis, sonophoresis, suction, electroporation, thermal poration, laser poration, passive diffusion, microfine (miniature) lances or cannulas, biolistic, subcutaneous implants or insertions, implanted sensing devices (e.g., in a body cavity, blood vessel, or under a surface tissue layer) as well as laser devices. In a preferred embodiment the method of extraction comprises use of a sampling device that provides transdermal extraction. In a preferred embodiment, the method of sensing the analyte, comprises use of a sensing device to obtain analyte-related signals. Examples of such sensing devices include, but are not limited to, a biosensor or an infrared sensor. In one embodiment of the present invention, the analyte comprises glucose. In one embodiment of the above methods, the analyte comprises glucose and said analyte monitoring system comprises a transdermal sampling device and a biosensor. In one embodiment of the above methods, one or more microprocessors are programmed to execute the methods. Additionally, said one or more microprocessors may be programmed to control said sampling and sensing devices. Further, the invention also includes an analyte monitoring system that employs any one or more of the above-described methods, said monitoring system comprising one or more microprocessors programmed to control a sampling device, a sensing device, data acquisition, and data manipulation associated with the methods.

These and other embodiments of the present invention will readily occur to those of ordinary skill in the art in view of the disclosure herein.

BRIEF DESCRIPTION OF THE FIGURES

FIGS. 3A, 3B, and 3C illustrate three different read frequencies schemes ranging from serial paired measurements (AB, AB, AB; FIG. 3A), to a "rolling value" measurement (AB, BA, AB, BA; FIG. 3B), to an "integral split" measurement, where readings are provided most frequently (FIG. 3C).

DETAILED DESCRIPTION OF THE INVENTION

Figure 1:
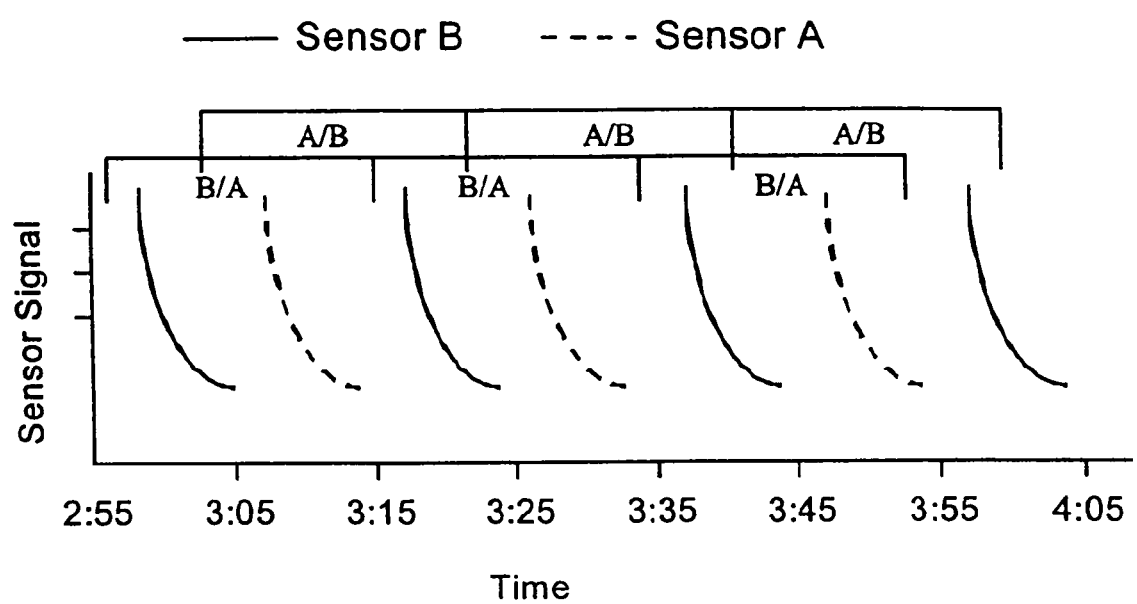
FIG. 1 presents a schematic diagram showing A and B biosensor signals, "B/A" averages and additional "moving average" ("A/B") measurement cycles for 6-readings-per-hour processing versus 3-readings-per-hour processing.

All publications, patents and patent applications cited herein are hereby incorporated by reference in their entireties.

1. Definitions

It is to be understood that the terminology used herein is for the purpose of describing particular embodiments only, and is not intended to be limiting. As used in this specification and the appended claims, the singular forms "a", "an" and "the" include plural referents unless the context clearly dictates otherwise. Thus, for example, reference to "a reservoir" includes a combination of two or more such reservoirs, reference to "an analyte" includes mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published 5, Sep. 1991; U.S. Pat. No. 5,636,632), suction, electroporation, thermal poration, passive diffusion (see, e.g., International Publication Nos.: WO 97/38126 (published 16, Oct. 1997); WO 97/42888, WO 97/42886, WO 97/42885, and WO 97/42882 (all published 20, Nov. 1997); and WO 97/43962 (published 27, Nov. 1997)), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88–93; International Publication WO 99/44507, published 1999 Sep. 10; International Publication WO 99/44638, published 1999 Sep. 10; and International Publication WO 99/40848, published Aug. 19, 1999). Iontophoretic sampling devices are described, for example, in International Publication No. WO 97/24059, published 10 Jul. 1997; European Patent Application EP 0942 278, published 15 Sep. 1999; International Publication No. WO 96/00110, published 4 Jan. 1996; International Publication No. WO 97/10499, published 2 Mar. 1997; U.S. Pat. Nos. 5,279,543; 5,362,307; 5,730,714; 5,771,890; 5,989,409; 5,735,273; 5,827,183; 5,954,685 and 6,023,629, 6,298,254, all of which are herein incorporated by reference in their entireties. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" refers to a system useful for obtaining frequent measurements of a physiological analyte present in a biological system. Such a system may comprise, but is not limited to, a sampling mechanism, a sensing mechanism, and a microprocessor mechanism in operative communication with the sampling mechanism and the sensing mechanism.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g, second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published 4 Jan. 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch® (Cygnus, Inc., Redwood City, Calif.) biographer glucose monitor (See, e.g., Tamada et al. (1999) JAMA 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," or "sensing mechanism," encompasses any device that can be used to measure the concentration or amount of an analyte, or derivative thereof, of interest. Preferred sensing devices for detecting blood analytes generally include electrochemical sensor devices, optical sensor devices, chemical sensor devices, and combinations thereof. Examples of electrochemical devices include the Clark electrode system (see, e.g., Updike, et al., (1967) Nature 214:986–988), and other amperometric, coulometric, or potentiometric electrochemical devices, as well as, optical methods, for example UV detection or infrared detection (e.g., U.S. Pat. No. 5,747,806). Other sensing devices include, but are not limited to, implanted sensing devices (e.g., in a body cavity, blood vessel, under skin, or under a surface tissue layer).

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric biosensors are described by Newman, J. D., et al. (1995) Analytical Chemistry 67:4594–4599. A sensing device may, for example, comprises one or more sensing electrodes. Alternately, a sensing device may, for example, comprise two or more sensing electrodes. In a further embodiment, a sensing device may, for example, comprise an array of sensing electrodes comprising greater than two electrodes.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal when an appropriate electrical bias is supplied, that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in WO 97/02811, published Jan. 30, 1997, and WO 0064533A1, published Nov. 2, 2000, both herein incorporated by reference. The ionically conductive material may comprise a biocide. For example, during manufacture of an autosensor assembly, one or more biocides may be incorporated into the ionically conductive material. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,735,273, 5,827,183, 6,141,573, and 6,201,979, all herein incorporated by reference.

The term "gel retaining layer" or "gel retainer" refers to a component of a collection assembly that is substantially planar and typically contacts both the collection insert layer and the electrode assembly.

The term "support tray" typically refers to a rigid, substantially planar platform and is used to support and/or align the electrode assembly and the collection assembly. The support tray provides one way of placing the electrode assembly and the collection assembly into the sampling system.

An "autosensor assembly" refers to a structure generally comprising a mask layer, collection insert layer, a gel retaining layer, an electrode assembly, and a support tray. The autosensor assembly may also include liners where the layers are held in approximate, functional relationship to each other. Exemplary collection assemblies and autosensor structures are described, for example, in International Publication WO 99/58190, published 18 Nov. 1999; and U.S. Pat. Nos. 5,735,273, 5,827,183, 6,141,573, and 6,201,979. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

"Parameter" refers to an arbitrary constant or variable so appearing in a mathematical expression that changing it give various cases of the phenomenon represented (McGraw-Hill Dictionary of Scientific and Technical Terms, S. P. Parker, ed., Fifth Edition, McGraw-Hill Inc., 1994). In the context of the GlucoWatch biographer, a parameter is a variable that influences the value of the blood glucose level as calculated by an algorithm.

"Decay" refers to a gradual reduction in the magnitude of a quantity, for example, a current detected using a sensor electrode where the current is correlated to the concentration of a particular analyte and where the detected current gradually reduces but the concentration of the analyte does not.

"Skip" or "skipped" signals refer to data that do not conform to predetermined criteria (for example, error-associated criteria as described in U.S. Pat. No. 6,233,471, herein incorporated by reference). A skipped reading, signal, or measurement value typically has been rejected (i.e., a "skip error" generated) as not being reliable or valid because it does not conform with data integrity checks, for example, where a signal is subjected to a data screen which invalidates incorrect signals based on a detected parameter indicative of a poor or incorrect signal.

2. General Overview of the Inventions

Before describing the present invention in detail, it is to be understood that this invention is not limited to particular types of microprocessors, monitoring systems, computational methods or process parameters, as use of such particulars may be selected in view of the teachings of the present specification. It is also to be understood that the terminology used herein is for the purpose of describing particular embodiments of the invention only, and is not intended to be limiting.

In one aspect the present invention relates to methods to increase the number of analyte-related signals used to provide analyte measurement values. Such analyte measurements may, for example, be chemical, physical, enzymatic, or optical. In one embodiment such analyte measurements are electrochemical, providing, for example, current and/or charge signals related to analyte amount or concentration. This aspect of the present invention typically applies to the situation where two or more analyte-related signals are used to obtain a single analyte measurement value, for example, the sum of two or more values may be correlated to an analyte amount or concentration, or an average of two or more values may be correlated to an analyte amount or concentration.

For example, in a two sensor system where analyte-related signals are serially obtained from each sensor in an alternating fashion, an analyte-related signal from the first sensor ($S_1$) may be summed with an analyte-related signal from the second sensor ($S_2$) to obtain a first analyte measurement value ($M_1$). The measurement cycle is repeated to obtain further analyte-related signals (e.g., $S_3$, $S_4$, $S_5$, $S_6$, etc.). In this example, $S_3$ and $S_4$ provide $M_2$, $S_5$ and $S_6$ provide $M_3$, etc. However, when applying the method of the present invention, the number of analyte-related measurement values is doubled. In the method of the invention each analyte-related signal is paired with its next neighbor to obtain a analyte measurement value, for example, $S_1$ and $S_2$ provide $M_1$, $S_2$ and $S_3$, provide $M_2$, $S_3$ and $S_4$ provide $M_3$, $S_4$ and $S_5$, provide $M_4$, etc. Thus the number of analyte-related measurement values is increased (in this example, essentially doubled).

In another aspect of the present invention, each analyte-related signal may be combined with one (or more) near or next neighbor to obtain, e.g., an average (or summed) analyte measurement value, i.e., the average (or summed value) may be obtained using more than two analyte-related signals. The number of analyte-related signals that are used to obtain, e.g., an average (or summed) value may be empirically determined by one of ordinary skill in the art following the guidance of the present specification. Generally, the averaged (or summed) analyte-related signal should be concordant with the trend of the measured analyte-related signals.

Another example involves a single sensor system. In this example, the analyte-related signals are serially obtained from a single sensor, for example, a first analyte-related signal ($S_1$), a second analyte-related signal ($S_2$), $S_3$, $S_4$, $S_5$, etc. The analyte related signals may be paired to obtain an analyte measurement value, for example, $S_1$ and $S_2$ provide $M_1$, $S_3$ and $S_4$ provide $M_2$, etc. In this case, the number of analyte-related measurement values may be increased by the method of the present invention by pairing each analyte-related signal with its next neighbor to obtain a analyte measurement value, for example, $S_1$ and $S_2$ provide $M_1$, $S_2$ and $S_3$, provide $M_2$, $S_3$ and $S_4$ provide $M_3$, $S_4$ and $S_5$, provide $M_4$, etc.

The present invention also relates to methods of increasing the number of analyte measurement values related to the amount or concentration of an analyte in a subject as measured using an analyte monitoring device. In this method a series of analyte-related signals is obtained from the analyte monitoring device over time. Typically, two or more contiguous analyte-related signals are used to obtain a single analyte measurement value (M). In this method, paired analyte-related signals are typically used to calculate the measurement value. One improvement provided by the present method is that, prior to the present method, such an analyte monitoring device typically used paired signals to obtain a single measurement value; but an analyte-related signal from the monitoring device was not typically used to calculate more than one analyte measurement value. In the present method, the two or more contiguous analyte-related signals, used to obtain the single analyte measurement value, comprise first and last analyte-related signals of the series.

The method involves mathematically computing rolling analyte measurement values, wherein (i) each rolling analyte measurement value is calculated based on two or more contiguous analyte-related signals from the series of analyte-related signals obtained from the analyte monitoring device. Subsequent rolling analyte measurement values are mathematically computed by dropping the first analyte-related signal from the previous rolling analyte measurement value and including an analyte-related signal contiguous and subsequent to the last analyte-related signal used to calculate the previous rolling analyte measurement value. Further rolling analyte measurement values are obtained by repeating the dropping of the first analyte-related signal used to calculate the previous rolling analyte measurement and including an analyte-related signal contiguous and subsequent to the last analyte-related signal used to calculate the previous rolling analyte measurement. Each rolling analyte measurement value provides a measurement related to the amount or concentration of analyte in the subject. By employing this method the number of analyte measurement values, derived from the analyte-related signals in the series of analyte-related signals obtained from the analyte monitoring device, is increased by serially calculating rolling analyte measurement values.

In one embodiment of this aspect of the invention, the rolling analyte measurement value is, for example, an average of two or more analyte-related signals; alternately, the rolling analyte measurement value is a sum of two or more analyte-related signals. In another embodiment, each analyte-related signal is represented by an integral over time, and the rolling analyte measurement value is obtained by integral splitting.

Missing or error-associated signals in the series of analyte-related signals obtained from the analyte monitoring device may be estimated using interpolation before mathematically computing rolling analyte measurement values. Such missing or error-associated signals may also be estimated using extrapolation before mathematically computing rolling analyte measurement values.

In a preferred embodiment, the analyte is glucose. In one embodiment, the analyte monitoring device comprises (i) an iontophoretic sampling device, and (ii) an electrochemical sensing device. The analyte-related signal may, for example, be a current or a charge related to analyte amount or concentration of analyte in the subject.

Other embodiments of the present invention will be clear to one of ordinary skill in the art in view of the teachings disclosed herein.

In another aspect of the present invention, interpolation and/or extrapolation are used to estimate unusable, missing or error-associated analyte-related signals. Such signals may be unusable for a variety of reasons, typically where an error has been detected that places an analyte-related signal in question. In the interpolation aspect, a previous analyte-related signal and a subsequent analyte-related signal are used to estimate the intervening analyte-related signal. Further, one or more previous analyte-related signals, and/or one or more subsequent analyte-related signals may also be employed for interpolation. In the extrapolation aspect, two previous analyte-related signals are used to estimate a subsequent analyte-related signal. Further, two or more previous analyte-related signals may also be employed for extrapolation. Interpolation and extrapolation of values is also employed in another aspect of the present invention that reduces the incident of failed calibrations.

One embodiment of this second aspect of the present invention includes a method of replacing unusable analyte-related signals when employing an analyte monitoring device to measure an analyte amount or concentration in a subject. A series of analyte-related signals, obtained from the analyte monitoring device over time, is provided wherein each analyte-related signal is related to the amount or concentration of analyte in the subject. An unusable analyte-related signal is replaced with an estimated signal, for example, by either:

(A) if one or more analyte-related signals previous to the unusable analyte-related signal and one or more analyte-related signals subsequent to the unusable analyte related signal are available, then interpolation is used to estimate the unusable, intervening analyte-related signal; or (B) if two or more analyte-related signals previous to the unusable analyte-related signal are available, then extrapolation is used to estimate the unusable, subsequent analyte-related signal.

In this method, the analyte monitoring device may comprise one or more sensor devices and a relationship between the signals obtained from the different sensor devices is used in interpolation and/or extrapolation calculation of estimated values. In one embodiment, the sensor device comprises two sensor elements and a ratio of signals obtained from a first sensor relative to a second sensor is employed in interpolation and/or extrapolation calculation of estimated signal values.

In a further aspect of the present invention, methods are described for reducing the incidence of failed calibration for an analyte monitoring system that is used to monitor an amount or concentration of analyte present in a subject.

In another aspect of the present invention, methods are described for providing an alert related to analyte values exceeding predetermined thresholds (e.g., high and/or low thresholds) or ranges of values. In this aspect of the invention a gradient method and/or predictive algorithm method may be used.

One or more microprocessors may be utilized to mathematically compute or control execution of algorithms related to any and all of the methods described herein. Further, such one or more microprocessors may be used to control operation of the components of the analyte monitoring system (e.g., a sampling device and/or a sensing device of the monitoring system). In addition, the one or more microprocessors may control operation of other components, further algorithms, calculations, and/or the providing of alerts to a subject (user of the analyte monitoring system).

The present invention also includes analyte monitoring devices employing the above methods.

Although a number of methods and materials similar or equivalent to those described herein can be used in the practice of the present invention, some preferred materials and methods are described herein.

3. Exemplary Monitoring Systems

Numerous analyte monitoring systems can be used in the practice of the present invention. Typically, the monitoring system used to monitor the level of a selected analyte in a target system comprises a sampling device, which provides a sample comprising the analyte, and a sensing device, which detects the amount or concentration of the analyte or a signal associated with the analyte amount or concentration in the sample.

One exemplary monitoring system (the GlucoWatch biographer) is described herein for monitoring glucose levels in a biological system via the transdermal extraction of glucose from the biological system, particularly an animal subject, and then detection of signal corresponding to the amount or concentration of the extracted glucose. Transdermal extraction is carried out by applying an electrical current or ultrasonic radiation to a tissue surface at a collection site. The electrical current is used to extract small amounts of glucose from the subject into a collection reservoir. The collection reservoir is in contact with a sensor element (e.g., a biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing a selected algorithm) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, frequently over a selected period of time. The collection reservoir is analyzed, at least periodically and typically frequently, to measure glucose concentration therein. The measured value correlates with the subject's blood glucose level.

Figure 2:
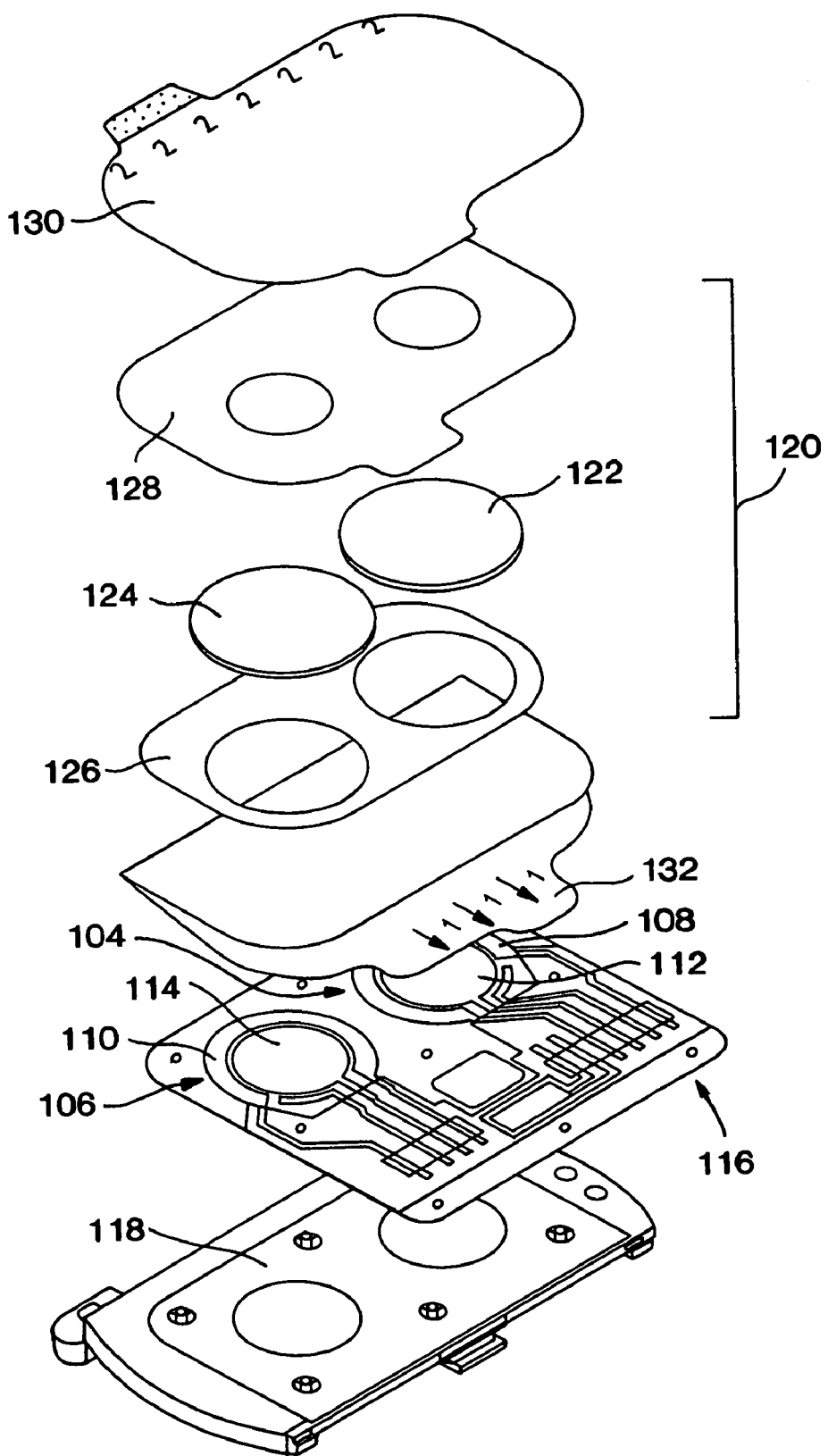
FIG. 2 presents a schematic of an exploded view of exemplary components comprising one embodiment of an autosensor for use in a monitoring system.

To sample the analyte, one or more collection reservoirs are placed in contact with a tissue surface on a subject. The ionically conductive material within the collection reservoir is also in contact with an electrode (for reverse iontophoretic extraction) which generates a current sufficient to extract glucose from the tissue into the collection reservoir. Referring to FIG. 2, an exploded view of exemplary components comprising one embodiment of an autosensor for use in an iontophoretic sampling system is presented. The autosensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In an alternative embodiment, the electrode assemblies can include bimodal electrodes. A mask layer 128 (for example, as described in PCT Publication No. WO 97/10356, published 20 Mar. 1997, and U.S. Pat. Nos. 5,735,273, 5,827,183, 6,141,573, and 6,201,979, all herein incorporated by reference) may be present. Other autosensor embodiments are described in WO 99/58190, published 18 Nov. 1999, herein incorporated by reference.

The mask and retaining layers are preferably composed of materials that are substantially impermeable to the analyte (e.g., glucose) to be detected (see, for example, U.S. Pat. Nos. 5,735,273, and 5,827,183, both herein incorporated by reference). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 2 are intended for use in a automatic sampling system which is configured to be worn like an ordinary wristwatch, as described, for example, in PCT Publication No. WO 96/00110, published 4 Jan. 1996, herein incorporated by reference. The wristwatch housing can further include suitable electronics (e.g., one or more microprocessor(s), memory, display and other circuit components) and power sources for operating the automatic sampling system. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc.

The sensing electrode can be, for example, a Pt-comprising electrode configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times. Some electrode embodiments are described in European Patent Publication 0 942 278 A2, published Sep. 15, 1999, herein incorporated by reference.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594–4599, 1995, herein incorporated by reference).

Any suitable iontophoretic electrode system can be employed, an exemplary system uses a silver/silver chloride (Ag/AgCl) electrode system. The iontophoretic electrodes are formulated typically using two performance criteria: (1) the electrodes are capable of operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also typically formulated using analytical- or electronic-grade reagents and solvents, and the polymer binder composition is selected to be free of electrochemically active contaminants which could diffuse to the biosensor to produce a background current.

Some exemplary sensors, electrodes, and electrode assemblies are described, for example, in the following United States patents, all herein incorporated by reference in their entireties: U.S. Pat. Nos. 5,954,685, 6,139,718, and 6,284,126.

The automatic sampling system can transdermally extract the sample over the course of a selected period of time using reverse iontophoresis. The collection reservoir comprises an ionically conductive medium, preferably the hydrogel medium described hereinabove. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electrical potential between the two electrodes to perform reverse iontophoresis in a manner known in the art. As discussed above, the biosensor selected to detect the presence, and possibly the level, of the target analyte (for example, glucose) within a reservoir is also in contact with the reservoir. Typically, there are two collections reservoirs, each comprising glucose oxidase, and each in operative contact with iontophoretic electrode and a sensing electrode. The iontophoretic electrode may be a bimodal electrode that also serves, non-concurrently, as a counter electrode to the sensing electrode (see, for example, U.S. Pat. No. 5,954,685, herein incorporated by reference).

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT Publication No. WO 96/00110, published 4 Jan. 1996, herein incorporated by reference. Typically, the electrical potential is alternated between two reservoirs to provide extraction of analyte into each reservoir in an alternating fashion (see, for example, U.S. Pat. Nos. 5,771, 890, 6,023,629, 5,954,685, 6,298,254, all herein incorporated by reference in their entireties). Analyte is also typically detected in each reservoir.

As an example, to extract glucose, the applied electrical current density on the skin or tissue can be in the range of about 0.01 to about 2 $mA/cm^2$. In order to facilitate the extraction of glucose, electrical energy can be applied to the electrodes, and the polarity of the electrodes can be, for example, alternated so that each electrode is alternately a cathode or an anode. The polarity switching can be manual or automatic. A device and method for sampling of substances using alternating polarity is described in U.S. Pat. No. 5,771,890, issued Jun. 30, 1998, herein incorporated by reference.

When a bimodal electrode is used (e.g., U.S. Pat. No. 5,954,685, issued Sep. 21, 1999, herein incorporated by reference), during the reverse iontophoretic phase, a power source provides a current flow to the first bimodal electrode to facilitate the extraction of the chemical signal into the reservoir. During the sensing phase, a separate power source is used to provide voltage to the first sensing electrode to drive the conversion of chemical signal retained in reservoir to electrical signal at the catalytic face of the sensing electrode. The separate power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s).

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (e.g., using a statistical technique or algorithm or combination of techniques) so that the system controller may display the subject's actual blood glucose concentration as measured by the sampling system. Such statistical techniques can be formulated as algorithm(s) and incorporated in one or more microprocessor(s) associated with the sampling system. Exemplary signal processing applications include, but are not limited to, those taught in the following U.S. Pat. Nos. 6,144,869, 6,233,471, 6,180,416, herein incorporated by reference. Exemplary methods for analyte monitoring include, but are not limited to, those taught in the following U.S. Pat. Nos. 5,989,409, 6,144,869, 6,272,364, 6,299,578, and 6,309,351, all herein incorporated by reference.

In a further aspect of the present invention, the sampling/sensing mechanism and user interface may be found on separate components (see, for example, WO 0047109A1, published Aug. 17, 2000). Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661, herein incorporated by reference), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841, herein incorporated by reference. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

4. Exemplary Analytes

The analyte can be any one or more specific substance, component, or combinations thereof that one is desirous of detecting and/or measuring in a chemical, physical, enzymatic, or optical analysis.

Analytes that can be measured using the methods of the present invention include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent.

In order to facilitate detection of the analyte, an enzyme (or enzymes) can be disposed within the one or more collection reservoirs. The selected enzyme is capable of catalyzing a reaction with the extracted analyte to the extent that a product of this reaction can be sensed, e.g., can be detected electrochemically from the generation of a current which current is,detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used singly (for detection of individual analytes) or together (for detection of multiple analytes), as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced or complemented with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea.

Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytoin), chemotherapy (e.g., adriamycin), hyperactivity (e.g., ritalin), and anti-organ-rejection (e.g., cyclosporin).

Preferably, a sensor electrode is able to detect the analyte that has been extracted into the one or more collection reservoirs when present at nominal concentration levels. Suitable exemplary biosensor electrodes and associated sampling systems as described in are described in PCT Publication Nos. WO 97/10499, published 20 Mar. 1997, WO 98/42252, published 1 Oct. 1998, U.S. Pat. No. 6,284, 126, and U.S. Pat. No. 6,139,718, all herein incorporated by reference.

A single sensor may detect multiple analytes and/or reaction products of analytes. For example, a platinum sensor could be used to detect tyrosine and glucose in a single sample. The tyrosine is detected, for example, by direct electrochemical oxidation at a suitable electrode potential (e.g., approximately 0.6V vs. Ag/AgCl ). The glucose is detected, e.g., using glucose oxidase and detecting the hydrogen peroxide reaction product.

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea.

5. Methods to Increase the Number of Analyte-Related Signals and Improve Usability A. "Rolling Values"

In one aspect, the present invention relates to methods to increase the number usable (i.e., good, as in not associated with a significant error) analyte related signals. In one embodiment the method provides for obtaining a series of samples comprising the analyte of interest, e.g., glucose, from a subject (e.g., a mammal). This method applies, generally, to monitoring systems that provide a series of analyte-related signals over time.

The present invention relates generally to a method for monitoring an amount or concentration of analyte present in a subject, wherein a series of signals, over time, is provided, and each signal is related to the analyte amount or concentration in the subject. Multiple signals are then combined to provide a "rolling value," for example by:

calculating a series of average signals wherein (i) each average signal is calculated based on two or more contiguous signals (i.e., signals next to or near in time or sequence to each other) in the series, and (ii) each average signal provides a measurement related to the amount or concentration of analyte in the subject; or calculating a series of sums, wherein (i) each summed signal is calculated based on two or more contiguous (i.e., next to or near in time or sequence) signals in the series, and (ii) each summed signal provides a measurement related to the amount or concentration of analyte in the subject. Missing signals in the series may be estimated using interpolation and/or extrapolation (discussed further below), and such estimated signals can be used in said calculations.

In one embodiment the invention relates to the use of a monitoring system comprising two or more sensors determining the analyte-related signals based on the same analyte. The method is described below with reference to the use of two collection reservoirs into which the analyte-containing samples are extracted. However, one of ordinary skill in the art, following the guidance of the present specification, could adapt this method for use with monitoring systems having one sensor or more than two sensors used to determine analyte-related signals.

In this exemplary method, two analyte-related signals are obtained from two independent sensors. For example, sensors in contact with extracted sample, comprising the analyte, are used to obtain a signal from each sample that is related to the analyte amount or concentration in the subject. Repeated rounds of extraction and sensing provide a series of signals. A sensing device may, for example, comprise first and second sensors, wherein the first sensor is in operative contact with the first collection reservoir and the sensing provides signal $S^A_j$ (where S is the signal, j is the time interval, for example a measurement half-cycle where a full measurement cycle comprises obtaining signal from sensor A and sensor B), and A denotes that the signal is from sensor A), and the second sensor is in operative contact with the second collection reservoir and the sensing provides signal $S^B_{j+1}$ (where S is the signal, j+1 is the time interval, for example a measurement half-cycle where a full measurement cycle comprises obtaining signal from sensor A and sensor B, e.g., a full measurement cycle is (j)+(j+1)), and B denotes that the signal is from sensor B).

Rather than basing the analyte-related measurement solely on $S^A/S^B$ pairs of signals, analyte-related measurements can be based on a rolling value of two (or more) signals in a series. For example, when using two contiguous signals, a series of rolling average signals may be calculated as follows:

$$(\text{average signal})_j = (S^B_{j-1} + S^A_j)/2, \quad \text{Eqn. 1}$$

where (j−1) is the measurement half-cycle previous to j;

$$(\text{average signal})_{j+1} = (S^A_j + S^B_{j+1})/2; \quad \text{Eqn. 2}$$

$$(\text{average signal})_{j+2} = (S^B_{j+1} + S^A_{j+2})/2, \quad \text{Eqn. 3}$$

where (j+2) is two measurement half-cycles after j; and, for each previous equation (Eqn.), wherein each average signal provides a measurement related to the amount or concentration of analyte in the subject. Calculation of further average signals at later (e.g., j+3, j+4, etc.) or earlier (e.g., j−1, j−2, etc.) times is accomplished following the procedure of the examples shown above.

Alternately, the sum or two or more signals may be related to analyte amount or concentration. In this case, a series of rolling values may be calculated, for example, when using two contiguous signals, as follows:

$$(\text{summed signal})_j = (S^B_{j-1} + S^A_j); \quad \text{Eqn. 4}$$

$$(\text{summed signal})_{j+1} = (S^A_j + S^B_{j+1}); \text{ and} \quad \text{Eqn. 5}$$

$$(\text{summed signal})_{j+2} = (S^B_{j+1} + S^A_{j+2}) \quad \text{Eqn. 6}$$

Calculation of further summed signals at later (e.g., j+3, j+4, etc.) or earlier (e.g., j−1, j−2, etc.) times is accomplished following the procedure of the examples shown above.

This method can be applied to data obtained using the GlucoWatch biographer. The GlucoWatch biographer comprises two sensing electrodes, designated "A" and "B", each in contact with a hydrogel. Current is passed across A and B for iontophoretic extraction of glucose. Each hydrogel is in contact with a sensor electrode, which provides signals related to glucose amount or concentration in a sample. After a sample is transdermally extracted into the hydrogel, the glucose in the sample reacts with the glucose oxidase within the hydrogel to produce hydrogen peroxide. The presence of hydrogen peroxide generates a current at the sensor electrode that is directly proportional to the amount of hydrogen peroxide in the hydrogel. This current provides a signal which can be detected and interpreted (for example, employing a Mixtures of Experts algorithm, see, for example, U.S. Pat. Nos. 6,180,416, 6,326,160, herein incorporated by reference in their entireties) by an associated system controller to provide a glucose amount or concentration value for display.

A current related to glucose amount or concentration in the sample (i.e., an analyte-related signal) is obtained at each sensor using a biosensor. Current may be converted to charge by integration. In the first version of the GlucoWatch biographer, each measurement cycle consisted of the following: 3 minutes of iontophoresis, followed by a 7 minutes of measurement for the first half cycle, then the iontophoresis current polarity was reversed and there was another 3 minutes of iontophoresis followed by 7 minutes of biosensor measurement. The glucose was drawn to the cathode, so in the first half cycle the "B" side collected glucose and in the second half cycle the "A" side collected glucose. The A and B measurements were averaged as one method to achieve noise reduction. Accordingly, one hour's worth of data involved three full cycles of BA averages: BA, BA, BA (FIG. 1). Using the method of the present invention, the averaging is done with a "leap frog" or rolling average approach, in which the last half cycle of a measurement becomes the first half cycle of the next measurement. One hour's worth of measurements can involve six full cycles of BA or AB averages: BA, AB, BA, AB, BA AB (FIG. 1). Thus the method provides the advantage of updating measurements more frequently to provide them to the user. Therefore, in the case of no skip-reading errors, measurements are reported based on signals from biosensors A and B measurement pairs such as: BA, AB, BA, AB, and so on.

The configuration of the GlucoWatch biographer included six extractions per hour, yet only three hourly readings. From an engineering standpoint, this represents a sub-optimum number of hourly readings. However, from the standpoint of a person with diabetes, and the number of readings cannot be said to be a sub-optimum as three hourly readings represent an unprecedented amount of information for subjects using the monitor. One solution to provide more hourly readings is to change the sequence of the GlucoWatch biographer to compute readings more frequently. The method described above computes six hourly readings corresponding to the six extractions. Advantages of the methods of the present invention for providing more measurement values include, but are not limited to, the following: allowing tighter screens for providing data points having minimum error; providing higher time/temporal resolution to more accurately portray data trends; providing a longer window for calibration; increasing the probability that a user can get trend data; and, providing more universal optimization due to larger pool of data.

The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

In one aspect of the present invention, one or more microprocessors employ an algorithm comprising one or more of the "rolling value" calculations described above. Typically, such one or more microprocessors are components of an analyte monitoring system.

As is apparent to one of skill in the art, various modification and variations of the above embodiments can be made without departing from the spirit and scope of this invention. Such modifications and variations are within the scope of this invention.

B. Interpolation/Extrapolation

In another aspect of the present invention, interpolation and/or extrapolation are used to estimate unusable, missing or error-associated analyte-related signals. Such signals may be unusable for a variety of reasons, typically where an error has been detected that places a detected analyte-related signal in question. Readings with such associated errors are typically "skipped." In the interpolation aspect, one or more previous analyte-related signals and one or more subsequent analyte-related signals are used to estimate an intervening analyte-related signal. In the extrapolation aspect, two or more previous analyte-related signals are used to estimate a subsequent analyte-related signal. Interpolation and extrapolation of values are also employed in another aspect of the present invention that reduces the incident of failed calibrations, described below. Exemplary methods are described below with reference to the use of two collection reservoirs into which the analyte-containing samples are extracted. However, one of ordinary skill in the art, following the guidance of the present specification, could adapt this method for use a single sensor or with more than two sensors used to determine analyte-related signals.

The interpolation and/or extrapolation methods of the present invention can be applied to single-sensor or multiple-sensor (i.e., two or more sensors) analyte monitoring systems. The following examples illustrate application of the methods of the present invention to a two-sensor system; however, modification of the method for application to analyte monitoring systems with a different number of sensors is within the ability of one of ordinary skill in the art in view of the teachings of the present specification.

In one aspect of the present invention, interpolation and/or extrapolation are used to estimate a skipped reading in a series of readings. For example, when using the rolling value described above, if an A or B reading is skipped (e.g., because of associated error), values surrounding (interpolation) or preceding (extrapolation) can be used to estimate the skipped value. The estimated value may then be combined with adjacent values to provide, for example, an average "A/B" reading or a summed "A/B" reading related to analyte amount or concentration.

Further, interpolation and extrapolation methods may be combined. For example, one missing reading may be provided by interpolation and then that reading may be used to in the extrapolation of another missing reading.

The present invention includes the use of relationships between the signals obtained from the sensors to perform interpolation and/or extrapolation of estimated values. For example, in a two sensor system a ratio of signals obtained from a first sensor relative to a second sensor may be employed in such interpolations and/or extrapolations to estimate values. Examples of methods of interpolation and/or extrapolation that can be used to provide estimated values are presented below.

In one embodiment, interpolation and/or extrapolation are used in a method for reducing the incidence of failed calibration for an analyte monitoring system. Calibration of analyte monitoring systems is often performed using a second, independent device. For example, in the case of the GlucoWatch biographer a calibration point relative to blood glucose concentration is provided by the user. The GlucoWatch biographer is put in place on the subject, allowed time to stabilize by performing several rounds of sampling and sensing, then the user uses an independent glucose monitor (for example performing a finger stick and using an optical detection system) to obtain a blood glucose value at a calibration time point. The calibration blood glucose value is entered into the GlucoWatch biographer by the user and the biographer associates the blood glucose value with its own sensor determinations of glucose amount for the same time point.

A series of samples is extracted from the subject using a sampling device. The extraction takes place alternately into a first collection reservoir and then into a second collection reservoir. Each sample comprises the analyte. In this example, the sampling device comprises first and second collection reservoirs and a measurement cycle refers to extracting into the first collection reservoir, extracting into said second collection reservoir, and sensing analyte in each collection reservoir. The sensing device is used to obtain a signal from each sample that is-related to the analyte amount or concentration in the subject, thus providing a series of signals. In this example the sensing device comprises a first sensor (A) and second sensor (B), wherein (1) the first sensor (A) is in operative contact with the first collection reservoir and the second sensor (B) is in operative contact with the second collection reservoir. Also, two consecutive signals comprise a measurement cycle, and each of the two consecutive signals is half-cycle signal.

A calibration method is performed to relate analyte amount or concentration in the subject to signals obtained from the sensors, where the calibration method comprises:

(i) obtaining a valid first half-cycle signal $S_j$, where a half-cycle signal $S_{j+1}$, or an estimate thereof, and a half-cycle signal $S_{j+2}$, or an estimate thereof, are both used in the calibration method so that the sensor signals correlate to the analyte amount or concentration in the subject, wherein the calibration method also employs an analyte calibration value that is independently determined;

(ii) providing the analyte calibration value; and (iii) selecting a conditional statement selected from the group consisting of:

(a) if neither the second half-cycle signal $S_{j+1}$ nor the third half-cycle signal $S_{j+2}$ comprise errors, then $S_{j+1}$ and $S_{j+2}$ are used in the calibration method;

(b) if only the second half-cycle signal $S_{j+1}$ comprises an error, then an estimated signal $S^E_{j+1}$ is obtained by determining an interpolated value using signal $S_j$ and $S_{j+2}$, wherein the interpolated value is $S^E_{j+1}$, and $S^E_{j+1}$ and $S_{j+2}$ are used in the calibration method;

(c) if only the third half-cycle signal $S_{j+2}$ comprises an error, then an estimated signal $S^E_{j+2}$ is obtained by determining an extrapolated value using signal $S_j$ and $S_{j+1}$, wherein the extrapolated value is $S^E_{j+2}$, and $S_{j+1}$ and $S^E_{j+2}$ are used in the calibration method; and (d) if both the second half-cycle signal $S_{j+1}$ and the third half-cycle signal $S_{j+2}$ comprise errors, then return to (i) to obtain a new, valid half-cycle signal $S_j$ from a later measurement half-cycle than the measurement half-cycle from which the previous, valid $S_j$ half-cycle signal was obtained.

This method can be applied to data obtained using the GlucoWatch biographer. When used in the GlucoWatch biographer this method of processing data reduces the incident of failed calibrations. The reduction was achieved by allowing calibrations in the presence of a "skip error" (i.e., when a signal is skipped) for only one of the two 10-minute sensor half-cycles at calibration. In this case, the sensor signal during the skipped period is estimated by a interpolation if it is the first half-cycle or extrapolation if it is the second half-cycle.

In one embodiment of the present invention, the calibration method begins when a non-skipped half-cycle has been successfully completed in order to attempt calibration. Therefore, a skipped half-cycle immediately before the expected opening of a "calibration window" causes the window to not open, or be "suppressed", until a half-cycle free of skip errors is completed. A calibration window refers to a period of time in which a user enters an independently determined analyte calibration value. In this embodiment of the invention, an un-skipped half-cycle is a gating requirement for the calibration process to be initiated. However, the method allows that estimated signals may be provided by interpolation or extrapolation should they be needed.

One benefit of the processing method is a decrease in aborted calibrations. Experiments performed in support of the present invention showed a reduction of more than 50% in aborted calibrations (not due to out-of-range entry) when the methods described herein were employed. When out-of-range entries were considered, a 21% decrease in failed calibrations was observed.

The processing method described herein for reducing the incidence of failed calibrations used three half-cycles, $S_j$, $S_{j+1}, S_{j+2}$ at calibration. In the absence of skip errors, signals from $S_{j+1}$ and $S_{j+2}$ were used to complete calibration. If either $S_{j+1}$ and $S_{j+2}$ (but not both) had a skip error, then a method of interpolations or extrapolations was invoked to estimate the signal at the skipped half-cycle. If both $S_{j+1}$ and $S_{j+2}$ contained skip errors, then a failed calibration resulted.

The interpolation method was invoked when calibration half-cycle $S_{j+1}$ had a skip error while $S_j$ and $S_{j+2}$ did not. Note that $S_j$ and $S_{j+2}$ were from the same sensor (A or B), while $S_{j+1}$ was from another sensor. One interpolation method, shown below in Eqn. 7A through Eqn. 7D, simply assumes that the estimated $S_{j+1}$ lies at a point on the line between $S_j$ and $S_{j+2}$, whose distance is related to the time interval between the points, with a correction for differences between Sensors A and B using an "AB ratio." In one embodiment of the present invention, the same AB ratio is used for interpolation and/or extrapolation regardless of the sensor source (i.e., A or B) of the signals being used to calculate the estimated (i.e., interpolated/extrapolated) signal value. In another embodiment of the present invention the form of the AB ratio used for interpolation and/or extrapolation depends on the sensor source (i.e., A or B) of the signals being used to calculate the estimated (i.e., interpolated/extrapolated) signal value. A further discussion of the AB ratio is presented below. An exemplary interpolation method follows here for a two sensor system where a different forms of the AB ratio are used depending on the source of the signals being used in the calculation.

In the situation where both $S_j$ and $S_{j+2}$ are signals from the B sensor ($S^B_j$ and $S^B_{j+2}$), and $S_{j+1}$ is being estimated for the A sensor signal ($S^{AE}_{j+1}$), interpolation Eqn. 7A may be employed as follows:

$$S^{AE}_{j+1} = \frac{A}{B}\left\{S^B_j + (S^B_{j+2} - S^B_j)\frac{(t_{j+1}-t_j)}{(t_{j+2}-t_j)}\right\} \qquad \text{Eqn. 7A}$$

wherein t is the time interval, for example, measurement half-cycle $t_j$, one subsequent half-cycle, $t_{j+1}$, or two subsequent half-cycles $t_{j+2}$. When the points are equally spaced, that is when $2(t_{j+1}-t_j)=(t_{j+2}-t_j)$, then Eqn. 7A reduces to the following Eqn. 7B:

$$S^{AE}_{j+1} = \frac{A}{B}\left(\frac{S^B_j + S^B_{j+2}}{2}\right) \qquad \text{Eqn. 7B}$$

In the situation where both $S_j$ and $S_{j+2}$ are signals from the A sensor ($S^A_j$ and $S^A_{j+2}$), and $S_{j+1}$ is being estimated for the B sensor signal ($S^{BE}_{j+1}$), interpolation Eqn. 7C may be employed as follows:

$$S^{BE}_{j+1} = \frac{B}{A}\left\{S^A_j + (S^A_{j+2} - S^A_j)\frac{(t_{j+1}-t_j)}{(t_{j+2}-t_j)}\right\} \qquad \text{Eqn. 7C}$$

When the points are equally spaced, that is when $2(t_{j+1}-t_j)=(t_{j+2}-t_j)$, then Eqn. 7C reduces to the following Eqn. 7D:

$$S^{BE}_{j+1} = \frac{B}{A}\left(\frac{S^A_j + S^A_{j+2}}{2}\right) \qquad \text{Eqn. 7D}$$

The extrapolation method was invoked when calibration half-cycle $S_{j+2}$ had a skip error while $S_j$ and $S_{j+1}$ did not. Note that $S_j$ and $S_{j+1}$ are from different sensors (A and B), while $S_{j+2}$ is from the same sensor as $S_j$. The extrapolation method, shown in the Eqn. 8A through Eqn. 8D, assumes the extrapolated point is on a line connecting $S_j$ and $S_{j+1}$, using a correction for differences between sensors A and B, and estimates a value for $S_{j+2}$. As noted above, a single AB ratio may be employed or the AB ratio may take different forms depending on the sensor source of the signals. Further discussion of the AB ratio is presented below. An exemplary interpolation method follows here for a two-sensor system where different forms of the AB ratio are used depending on the source of the signals being used in the calculation.

In the situation where $S_j$ is signal from sensor A ($S^A_j$) and $S_{j+1}$ is signal from B sensor ($S^B_{j+1}$), and $S_{j+2}$ is being estimated for the A sensor signal ($S^{AE}_{j+2}$), extrapolation Eqn. 8A may be employed as follows:

$$S^{AE}_{j+2} = \frac{A}{B}(S^B_{j+1}) + \left[\left\{\frac{A}{B}(S^B_{j+1}) - S^A_j\right\}\frac{(t_{j+2}-t_{j+1})}{(t_{j+1}-t_j)}\right] \qquad \text{Eqn. 8A}$$

When the points are equally spaced, that is when $(t_{j+2}-t_{j+1})=(t_{j+1}-t_j)$, then Eqn. 8A reduces to the following Eqn. 8B:

$$S^{AE}_{j+2} = 2\frac{A}{B}S^B_{j+1} - S^A_j \qquad \text{Eqn. 8B}$$

In the situation where $S_j$ is signal from the B sensor ($S^B_j$) and $S_{j+1}$ is signal from the A sensor ($S^A_{j+1}$), and $S_{j+2}$ is being estimated for the B sensor signal ($S^{BE}_{j+2}$), extrapolation Eqn. 8C may be employed as follows:

$$S^{BE}_{j+2} = \frac{B}{A}(S^A_{j+1}) + \left[\left\{\frac{B}{A}(S^A_{j+1}) - S^B_j\right\}\frac{(t_{j+2}-t_{j+1})}{(t_{j+1}-t_j)}\right] \qquad \text{Eqn. 8C}$$

When the points are equally spaced, that is when $(t_{j+2}-t_{j+1})=(t_{j+1}-t_j)$, then Eqn. 8C reduces to the following Eqn. 8D:

$$S^{BE}_{j+2} = 2\frac{B}{A}S^A_{j+1} - S^B_j \qquad \text{Eqn. 8D}$$

The interpolation and extrapolation methods described above use a relationship between the signals of sensor A and B. One method of determining this relationship is to calculate a weighted average using a smoothing protocol. Smoothing methods that may be employed include, but are not limited to, (i) taking a basic average of all available ratios, (ii) initializing the processing method with the ratio at some specific point, (iii) trend methods, and (iv) methods including exponential components. One exemplary smoothing protocol useful in the practice of the present invention is the Holt-Winters smoothing (examples corresponding to the ratios used above are shown in Eqn. 9A and Eqn. 9B).

$$\left(\frac{A}{B}\right)_{s,i} = w\left(\frac{A}{B}\right)_i + (1-w)\left(\frac{A}{B}\right)_{s,i-1} \quad \text{Eqn. 9A}$$

$$\left(\frac{B}{A}\right)_{s,i} = w\left(\frac{B}{A}\right)_i + (1-w)\left(\frac{B}{A}\right)_{s,i-1} \quad \text{Eqn. 9B}$$

In Eqn. 9A and Eqn. 9B, $(A/B)_{s,i}$ and $(B/A)_{s,i}$ refer to "smoothed" AB ratios for measurement cycle i, $(A/B)_i$ and $(B/A)_i$, refer to the AB ratio for measurement cycle i, and $(A/B)_{s,i-1}$ and $(B/A)_{s,i-1}$, refer to the smoothed AB ratio from the previous measurement cycle i−1. In the Holt-Winters smoothing presented above, the determination of the smoothed AB ratio depends on the adjustable parameter w (a weighting factor). Experiments performed in support of the present invention were carried out on the sensor signals at early times for the GlucoWatch biographer. Predictions of sensor signal were generated at all potential points with both interpolation and extrapolation. For those points where an actual sensor signal was available, a relative error was calculated. The mean relative absolute relative error (MARE) was found for each sensor for each method at each smoothing weight. Based on an initial analysis a smoothing weight 0.7 (i.e., 70%) was chosen. Other smoothing weights may be employed where w is a smoothing factor and represents a numerical, percentage value between and inclusive of 0 to 100%, where w is represented by a fraction between and inclusive of 0 to 1.

Experiments performed in support of the present invention suggest that a reduction of failed calibrations is the main impact of the new processing method, thus resulting in better "usability" of the GlucoWatch biographer, in the sense that the number of finger-pricks required for calibration (i.e., the analyte calibration valued independently obtained) is greatly reduced.

The smoothed AB ratios described above were used in the interpolation and extrapolation of skipped half-cycle signals, e.g., at calibration. Smoothing is not essential and in some applications a fixed AB ratio may be employed. It was initially assumed that the smoothed B/A ratio would be reciprocal of the smoothed A/B ratio. When this is the case a single AB ratio may be used. However, experiments performed in support of the present invention that employed the GlucoWatch biographer indicated that the smoothed B/A ratio was not mathematically equivalent to the reciprocal of the smooth A/B ratio and that in some applications use of separate smoothed A/B and B/A ratios (as shown above) provides more reliable results for the interpolation and extrapolation of both sensors, e.g., at calibration.

The processing methods discussed above are optimal when both A/B and B/A ratios are calculated separately for each consecutive non-skip B cathode and A cathode half-cycles. As new A/B and B/A ratios are calculated for news cycles, the most recent one is smoothed with the previous one. One exemplary smoothing method is performed according to the-following general equation (Eqn. 10):

$$R_i^s = wR_i + (1-w)R_{i-1}^s \quad \text{Eqn. 10}$$

wherein, $R_i$ is the A/B or B/A ratio for a $i^{th}$ measurement cycle, $R^S_i$ is smoothed R for a $i^{th}$ measurement cycle, and w is a smoothing factor and represents a numerical, percentage value between and inclusive of 0 through 100%, where w is represented by a fraction between and inclusive of 0 through 1, and $R^S_{i-1}$ is a smoothed ratio for the $(i-1)^{th}$ measurement cycle, wherein the $i^{th}$ measurement cycle is composed of first and second half-cycles and the second half-cycle value of the $i^{th}$ measurement cycle precedes $S_j$. A single $R^S_j$ may be used or more than one such ratio may be employed.

The smoothed ratios of A/B and B/A are stored and used for an interpolation and extrapolation of skipped cycle intervals, e.g., during calibrations.

In order to compare interpolation and/or extrapolation estimates using a single AB ratio versus methods employing separate A/B and B/A ratios, a calibration cycle with interpolation and extrapolation was simulated without specifying the identity of the A and B sensors. Then each sensor was arbitrarily assigned to A or B. When a single AB ratio was maintained (single AB ratio method), the interpolation an extrapolation results are dependent on which sensor was assigned A and which sensor was assigned B. When separate A/B and B/A ratios were maintained (separate A/B and B/A ratio method), the interpolation and extrapolation results were identical when the A and B sensor assignments were switched. This simulation suggested that calculating separate A/B and B/A ratios was more accurate than using a single AB ratio. However, using a single AB ratio still provides an efficacious means for calculating estimated values.

Experiments performed in support of the present invention suggest that minor inconsistencies in interpolation and extrapolation calculations that resulted from the use of a single smooth AB ratio for both the A and B sensors was eliminated when separate smoothed A/B and B/A ratios are maintained.

In this modification of methods of making interpolation and/or extrapolation estimates of the present invention, the A/B ratio and B/A ratio can, for example, store ratios on the A and B signal integrals from the later part of the equilibration period. They are then used as needed interpolation and/or extrapolation of skipped signals.

In the context of the methods of the present invention for reducing the number of failed calibrations applied to the GlucoWatch biographer, an acceptable A/B (and B/A) ratio is generated if there is a least one pair of consecutive non-skipped A and B signals prior to this first good half-cycle signal that begins the calibration. Until good A/B and B/A ratios are available, a biographer employing the methods of the present invention does not open a calibration window and calibration will not be performed.

If more than one pair is available, then a smoothing technique may be used to obtain a rolling value (for example, as shown in Eqn. 10, above):

$$R_i^s = wR_i + (1-w)R_{i-1}^s \quad \text{Eqn. 10}$$

where R is the A/B ratio or B/A ratio, the smoothing factor w represents a numerical, percentage value between and inclusive of 0 to 100%, where w is represented by a fraction between and inclusive of 0 to 1. To maximize consistency with signals from the A and B sensors and for calculation of skipped integrals, separate A/B and B/A ratios are maintained for use in the ratio smoothing equation. The AB and BA ratios may be maintained after calibration for use, for example, during recalibration or for interpolation and/or extrapolation of later missing values. The ratios may be updated after each pair of consecutive non-skipped A and B signals.

As discussed above, the interpolation method is invoked when calibration half-cycle $S_{j+1}$ has a skip error while $S_j$ and $S_{j+2}$ do not. Note that $S_j$ and $S_{j+2}$ are from the same sensor (A or B), while $S_{j+1}$ is from the other sensor. The interpolation method, shown above, assumes that $S_{j+1}$ lies at the vertical midpoint between $S_j$ and $S_{j+2}$, and is then corrected for Sensor A to B differences by as follows: when interpolating for the A sensor ($S_{j+1}$ is the A sensor), the A/B ratio is used. When interpolating for the B sensor ($S_{j+1}$ is the B sensor), the B/A ratio is used.

Also as discussed above, the extrapolation method is invoked when calibration half-cycle $S_{j+2}$ has a skip error while $S_j$ and $S_{j+1}$ do not. Note that $S_j$ and $S_{j+1}$ are from different sensors (A and B), while $S_{j+2}$ is from the same sensor as $S_j$. The extrapolation method, shown above, makes essentially the same assumptions as the interpolation method, but solves for $S_{j+2}$. When extrapolating for the A sensor the Ratio$_{ab}$ factor is equal to the A/B ratio. When extrapolating for B sensor the Ratio$_{ab}$ factor is equal to the B/A ratio.

The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

Further, experiments performed in support of the present invention that utilize the GlucoWatch biographer have indicated that skipped signals tend to occur in clusters. Accordingly, one aspect of the present invention comprises waiting for an unskipped (i.e., error free or good signal) half-cycle signal before initiating a calibration sequence (e.g., before opening a calibration window inviting the user to provide an independently determined analyte calibration value). Such an independently determined analyte calibration value may be obtained, for example, by using a traditional blood glucose measuring device, e.g., blood glucose amounts as determined using a OneTouch® (Johnson & Johnson, New Brunswick, N.J.) blood glucose monitoring device.

Although the above-methods have been exemplified for two sensors, the methods can be applied to single-sensor or multiple-sensor (i.e., two or more sensors) devices by one of ordinary skill in the art in view of the teachings of the present specification.

The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

In one aspect of the present invention, one or more microprocessors employ an algorithm comprising one or more of the interpolation, extrapolation, and/or A/B ratio calculations described above. Typically, such one or more microprocessors are components of an analyte monitoring system.

As is apparent to one of skill in the art, various modification and variations of the above embodiments can be made without departing from the spirit and scope of this invention. Such modifications and variations are within the scope of this invention.

C. Integral Splitting

One extension of using "rolling values" to increase frequency of readings is to use subsets of each trapezoidal integral (i.e., integral splitting) to update the signal after each biosensor current reading is taken. For example, when each analyte-related signal is represented by an integral over time, rolling analyte measurement values may be obtained by integral splitting. In this way, the readings are reported to the user as new information is obtained. This allows readings to be given as often as current readings can be taken, which may be, for example, as often as more than once per second. FIGS. 3 and 4 illustrate the concept of integral splitting. In FIGS. 3A to 3C, three different read frequencies schemes are shown that range from serial paired measurements (AB, AB, AB; FIG. 3A), to a "rolling value" measurement (AB, BA, AB, BA; FIG. 3B), and finally an "integral split" measurement (FIG. 3C), where readings are provided most frequently. In this nomenclature, the numbers in parentheses are "ranges" of trapezoidal segments used for each measurement (e.g. A2(2–N)A3(1)B2 means to use the entire B2 integral, along with the first segment of the A3 and from segment 2 to N of A2 with N being the total number of segments)—these expressions are not mathematical formulae.

Figure 4A:
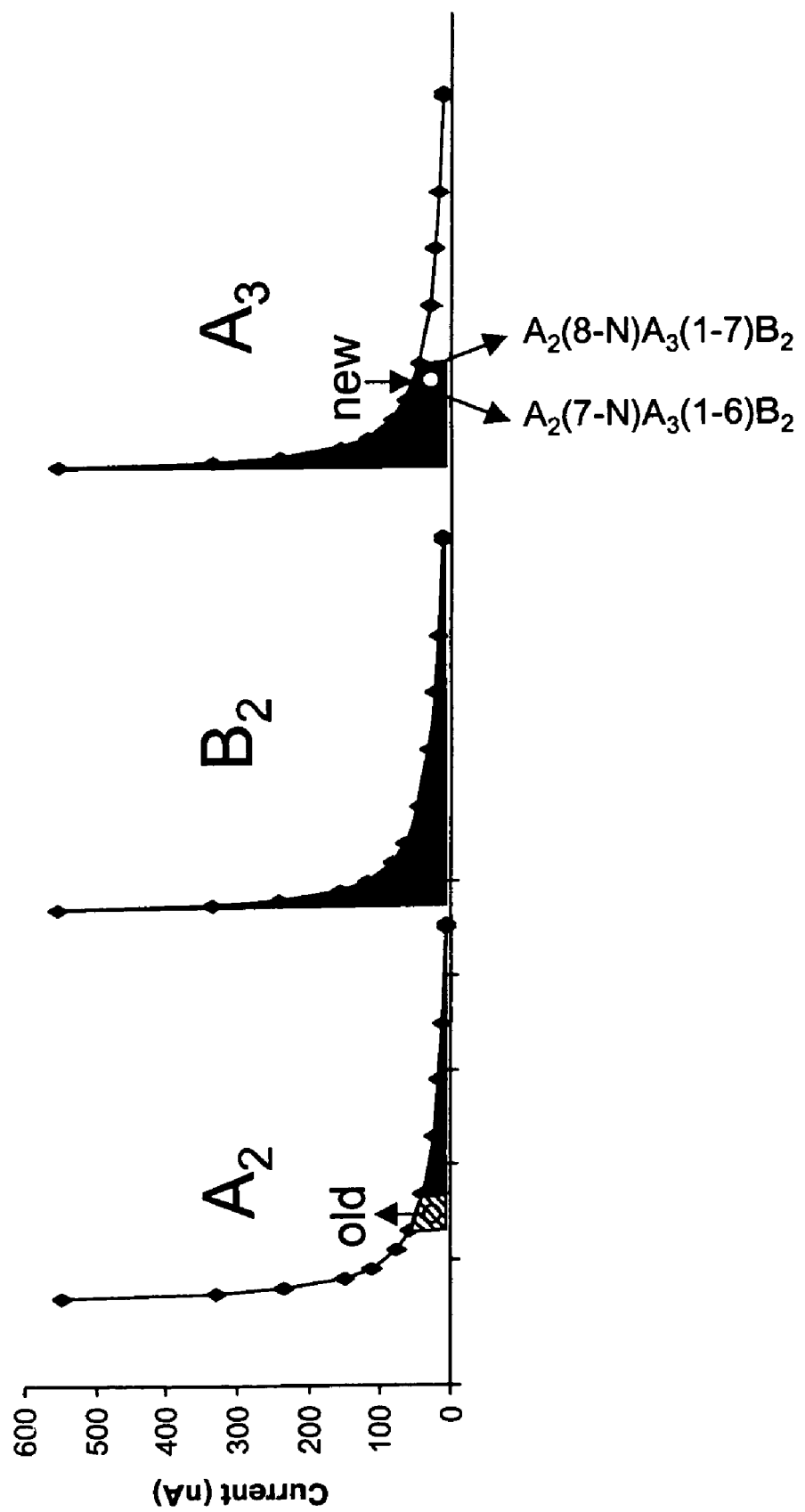
FIG. 4A illustrates how the newest trapezoidal segment replaces the oldest one as a new current value is taken in the integral splitting method.
Figure 4B:
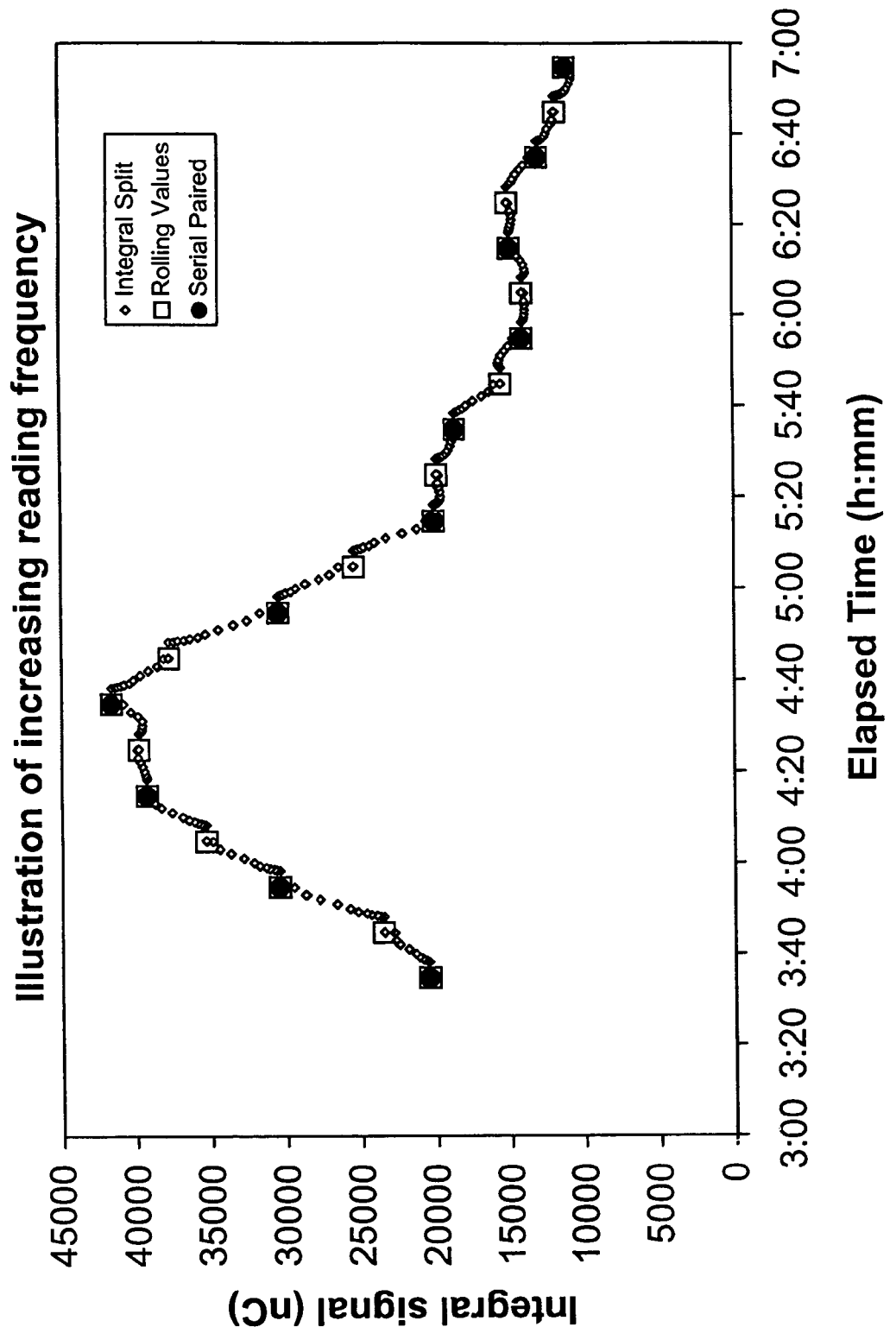
FIG. 4B illustrates the increase in reading frequency for various measurement methods (e.g., integral splitting and rolling values relative to serial paired).

In FIG. 4A, an example is shown of how the newest trapezoidal segment replaces the oldest one as a new current value is taken. In this example, the eighth sensor reading completes the seventh trapezoidal segment of Integral A3. This segment A3(7) replaces A2(7), so that the final signal used for calculation changes from A2(7–N)A3(1–6)B2 to A2(8–N)A3(1–7)B2. FIG. 4B is an illustration of the increase in reading frequency for various measurement methods described above (e.g., integral splitting and rolling values relative to serial paired).

The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

In one aspect of the present invention, one or more microprocessors employ an algorithm comprising integral splitting calculations as described above to provide readings as often as current readings can be taken. Typically, such one or more microprocessors are components of an analyte monitoring system.

As is apparent to one of skill in the art, various modification and variations of the above embodiments can be made without departing from the spirit and scope of this invention. Such modifications and variations are within the scope of this invention.

D. Recalibration Methods (i) Optional Recalibrations

Figure 5:
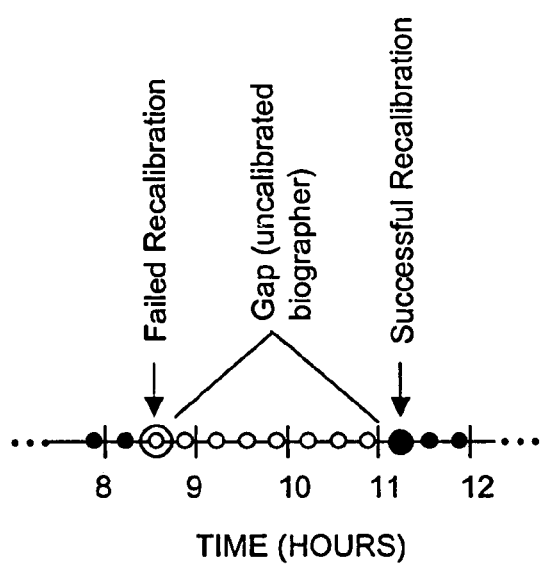
FIG. 5 illustrates a situation wherein analyte readings are missed by an analyte monitoring system following a failed recalibration attempt, until a successful recalibration is performed.

The following recalibration methods are described with reference to the GlucoWatch biographer, however, in view of the teachings of the present specification one of ordinary skill in the art can apply these recalibration methods to any analyte monitoring system that provides a series of analyte readings dependent on obtaining a calibration value. As described above, the GlucoWatch biographer is an exemplary analyte monitoring system where the analyte of interest is glucose. In the GlucoWatch biographer, a user is able to recalibrate the GlucoWatch biographer at any time if, for example, the GlucoWatch biographer readings are inconsistent with the user's physical symptoms or if the user receives a number of SKIP messages (i.e., messages relating to data that do not conform to predetermined criteria (for example, error-associated criteria as described in U.S. Pat. No. 6,233,471, herein incorporated by reference). In the GlucoWatch biographer, if the user decides to recalibrate the GlucoWatch biographer and is unsuccessful for any reason (for example, due to SKIP errors or out-of-range entry), the previously entered calibration is terminated and the GlucoWatch biographer reverts to an uncalibrated state. The GlucoWatch biographer is then only able to generate glucose readings if the re-calibration entry is successful. This situation can potentially lead to long periods of time in which the user receives no glucose readings. This situation is illustrated in FIG. 5.

Figure 6:
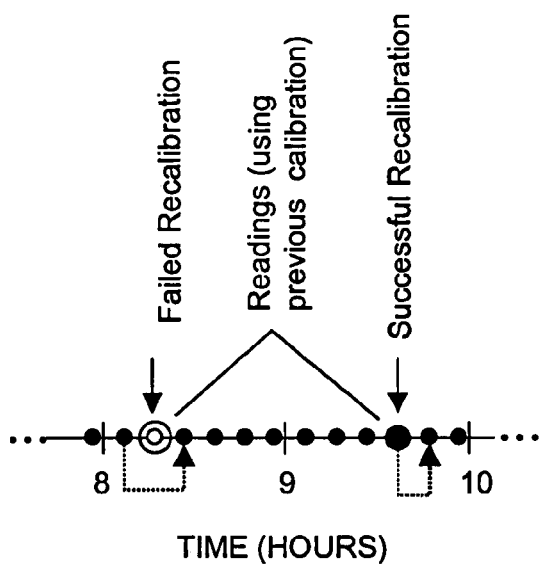
FIG. 6 illustrates a situation wherein analyte readings are not missed by an analyte monitoring system following a failed recalibration attempt because the system reverts to using a previous calibration until a successful recalibration is performed.

A useful modification of the above-described recalibration feature is that during a failed optional recalibration, the glucose monitoring system can continue to generate glucose readings using the previously accepted calibration value while the glucose monitoring system assesses the entered re-calibration value. Once the entered, re-calibration value is accepted, the glucose monitoring system begins to generate glucose readings using the new calibration value. This situation is illustrated in FIG. 6.

(ii) Consecutive Skipped Measurements and Required Re-Calibration

The following recalibration methods are described with reference to the GlucoWatch biographer, however, in view of the teachings of the present specification one of ordinary skill in the art can apply these recalibration methods to any analyte monitoring system that provides a series of analyte readings dependent on obtaining a calibration value. If the GlucoWatch biographer produces six consecutive skipped readings, then the GlucoWatch biographer aborts the sequence and the user must change the AutoSensor and perform a warm-up and calibration period before the GlucoWatch biographer will produce glucose measurements again. The sequence is aborted and the measurement period is terminated early, for example, to safeguard against potentially inaccurate readings. When the sequence aborts, the GlucoWatch biographer sounds a distinctive beep, and an error message is displayed. Additional research has shown that the number of consecutive skips may be increased from six to eighteen without reducing the safety or effectiveness of the device.

In addition to increasing the number of allowable consecutive skips, rather than aborting the sequence, the user may be asked to re-calibrate the device after, for example, eighteen consecutive skips. After eighteen consecutive skips, the analyte monitoring system removes the original calibrations value and requests a new conventional meter blood glucose measurement. This is termed "Required Re-Calibration. " During Required Re-Calibration, the user engages the same calibration process that is normally performed at the end of a warm-up period. For this Re-Calibration method, the calibration integrity checks (interpolation and/or extrapolation, suppression) are applied to re-calibrating the analyte monitoring device.

Accordingly, for an analyte monitoring system that requires calibration, a number of consecutive skips can be determined that still allows the analyte monitoring system to provide safe and effective readings. After the number of consecutive skips is met or exceeded one or more microprocessors of the analyte monitoring system may be programmed to force a required recalibration.

The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

In one aspect of the present invention, one or more microprocessors employ an algorithm comprising programmed instructions to execute the above described recalibration methods. Typically, such one or more microprocessors are components of an analyte monitoring system.

As is apparent to one of skill in the art, various modification and variations of the above embodiments can be made without departing from the spirit and scope of this invention. Such modifications and variations are within the scope of this invention.

6. Methods of Providing an Analyte Concentration-Related Alert

Following here two approaches are described to provide an analyte concentration-related alert when an analyte level falls above or below predetermined thresholds or outside of a predetermined range of reference values: gradient methods and predictive algorithm methods. These methods provide for predicting an analyte concentration-related event in a subject being monitored for levels of a selected analyte. Exemplary analyte concentration-related alerts include, but are not limited to, a "down alert," that is an alert when an analyte levels falls below a predetermined value or range of values (e.g., a hypoglycemic alert), and an "up alert," that is, an alert is provided when an analyte level falls above a predetermined value or range of values (e.g., a hyperglycemic alert).

The gradient method employs the current and the past analyte monitoring system reading and determines the rate of decline and/or increase. The rate of change of the analyte (e.g., a rate of change of the analyte in the direction of decreasing amount of analyte) in the subject is then used to determine whether to alert the subject or not. One limitation of this method in the context of glucose monitoring is that, when this method is used alone for the prediction of, e.g., a hypoglycemic event, it would trigger the down alert even at very high blood glucose levels when the rate of decline exceeded the acceptable, predetermined rate of change.

The predictive algorithm method uses a predictive algorithm to predict the next analyte reading based on previously obtained analyte readings (e.g., obtained using the GlucoWatch biographer). Based on the value of this predicted reading relative to predetermined threshold values or range of values, the analyte concentration-related alert would or would not be triggered. The gradient method and the predictive algorithm method may be combined. One preferred embodiment is discussed below where the gradient method is combined with the predictive algorithm method. Further, such a combination method may be combined with individual predictors (such as, skin conductivity and temperature).

A. The Gradient Method

Several models for the determination of a gradient (i.e., the rate of change) are as follows:

Model A: $\frac{y_{(n)} - y_{(n-1)}}{\Delta t}$ (concentration/time); where $\Delta t = (t_{(n)} - t_{(n-1)})$ Model B: $\frac{y_{(n)} - y_{(n-1)}}{y_{(n-1)} \Delta t}$ (fractional change/time); where $\Delta t = (t_{(n)} - t_{(n-1)})$ Model C: $\frac{y_{(n)} - y_{(n-2)}}{\Delta t}$ (concentration/time); where $\Delta t = (t_{(n)} - t_{(n-2)})$ -continued Model D: $\frac{y_{(n)} - y_{(n-2)}}{y_{(n-2)}\Delta t}$ (fractional change/time); where $\Delta t = (t_{(n)} - t_{(n-2)})$ Model E: Average$\left[\frac{y_{(n)} - y_{(n-1)}}{\Delta t_1}, \frac{y_{(n-1)} - y_{(n-2)}}{\Delta t_2}, \frac{y_{(n)} - y_{(n-2)}}{\Delta t_3}\right]$ (concentration/time);

where $\Delta t_1 = (t_{(n)} - t_{(n-1)})$, $\Delta t_2 = (t_{(n-1)} - t_{(n-2)})$, and $\Delta t_3 = (t_{(n)} - t_{(n-2)})$. In this model, the average is of all three values shown in the brackets.

Model F: $\frac{y_{(n)} - y_{(n-3)}}{y_{(n-3)}\Delta t}$ (fractional change/time); where $\Delta t = (t_{(n)} - t_{(n-3)})$ In the above models, $y_n$ stands for an analyte reading at time point $t_{(n)}$, $y_{(n-1)}$ an analyte reading at time point $t_{(n-1)}$ (i.e., the previous reading to $y_n$), $y_{(n-2)}$ an analyte reading at time point $t_{(n-2)}$ (i.e., the reading previous to $y_{(n-1)}$), $y_{(n-3)}$ an analyte reading at time point $t_{(n-3)}$ (i.e., the reading previous to $y_{(n-2)}$). Each of the above methods give a rate of change. Models A, C, and E give concentration change per time interval, for example, the units may be mg/dL/minute or mmol/L/minute when y is a glucose reading. Models B, D, and F give a fractional change per time interval (e.g., percentage change in the glucose reading per minute). When using a gradient method a threshold of an acceptable rate of change is selected (for example, based on experimental data and/or acceptable ranges of measurement values).

In one embodiment, a microprocessor employs an algorithm comprising the selected model and calculates the rate of change (e.g., in the indicated units). The microprocessor then employs an algorithm to compare the calculated rate of change to a predetermined acceptable rate of change. If the calculated rate of change differs significantly from the acceptable rate of change then the microprocessor triggers the analyte monitoring system to provide an alert to the user. For example, applying Model D to glucose readings in order to predict a hypoglycemic event an acceptable rate of change may be established as a decrease of 1.75%/min for $\Delta t = 20$ min. If the rate of change exceeds a decrease of 1.75%/min for $\Delta t = 20$ min then the subject is alerted to this fact (e.g., by an audible alert and/or a prompt on the user interface).

Typically when employing the gradient models, to provide a low-analyte alert (e.g., hypoglycemic event alert) the calculated rate of change is negative and less than the predetermined threshold rate of change (e.g., a calculated rate of change of negative 2%/min for $\Delta t = 20$ minutes is less than the threshold value of negative change of 1.75%/min for $\Delta t = 20$ min); and/or to provide a high-analyte alert (e.g., hyperglycemic event alert) the calculated rate of change is positive and greater than the predetermined threshold rate of change (e.g., a calculated rate of change of 2%/min for $\Delta t = 20$ minutes is greater than the threshold value of change of 1.75%/min for $\Delta t = 20$ min). Alternatively, absolute values of the calculated and threshold rates of change may be used for comparison. In this case, an alert is provided when the absolute value of the calculated rate of change is greater than the absolute value of predetermined threshold rate of change.

In addition to the above-described gradient models, a number of other models can be employed in a gradient method, including, but not limited to, use of a regression model to determine the gradient, using, for example, a best-fit function.

B. The Predictive Algorithm Method

One predictive algorithm method (Eqn. 11) has been previously described for use in time-series predictions (U.S. Pat. No. 6,272,364, herein incorporated by reference in its entirety). Several other predictive algorithm methods follow here as well.

$$y_{(n+1)} = y_{(n)} + \alpha(y_{(n)} - y_{(n-1)}) + \frac{\alpha^2}{2}(y_{(n)} - 2y_{(n-1)} + y_{(n-2)}) \quad \text{Eqn. 11}$$

$$y_{(n+1)} = y_{(n)} + \frac{(y_{(n)} - y_{(n-1)})}{(t_n - t_{(n-1)})} * (t_{(n+1)} - t_n) \quad \text{Eqn. 12}$$

$$y_{(n+1)} = \frac{5}{2}y_{(n)} + -2(y_{(n-1)}) + \frac{1}{2}(y_{(n-2)}) \quad \text{Eqn. 13}$$

$$y_{(n+2)} = y_{(n)} + \frac{(y_{(n)} - y_{(n-2)})}{(t_n - t_{(n-2)})} * (t_{(n+2)} - t_n) \quad \text{Eqn. 14}$$

$$y_{(n+2)} = y_{(n)} + \frac{(y_{(n)} - y_{(n-1)})}{(t_n - t_{(n-1)})} * (t_{(n+2)} - t_n) \quad \text{Eqn. 15}$$

In these equations, the methods calculate the predicted value of a variable y (e.g., concentration of analyte) at time $t_{n+1}$ (or $t_{n+2}$, as indicated) as a function of that variable at the current time $t_n$, as well as at a previous time or times, e.g., $t_{n-1}$ and/or $t_{n-2}$). In these equations, $y_{(n+1)}$ and $y_{(n+2)}$ are predicted values of variable y at time points (n+1) and (n+2), respectively, $y_{(n)}$, $y_{(n-1)}$, $y_{(n-2)}$ are analyte-related values at times (n), (n−1), and (n−2), respectively, $t_{(n-2)}$, $t_{(n-1)}$, $t_{(n)}$, $t_{(n+1)}$, $t_{(n+2)}$, are time points at times (n−2), (n−1), (n), (n+1) and (n+2), respectively. In Eqn. 11, $\alpha$ is an empirically determined weighting value that is typically a real number between 0 and 1. Each of the above methods provides a predicted analyte value, for example, an amount or concentration (e.g., the units may be mg/dL (milligrams of glucose per deciliter) or mmol/L when y is a glucose reading). When using a predictive algorithm thresholds of an acceptable range for analyte amount or concentration are selected (for example, based on experimental data and/or acceptable ranges of measurement values). High threshold values may be selected (e.g., a glucose value that is considered hyperglycemic for a subject), low threshold values may be selected (e.g., a glucose value that is considered hypoglycemic for a subject), and/or an acceptable range of values with an associated error may also be employed.

In one embodiment, one or more microprocessors employ an algorithm comprising the selected predictive algorithm and calculates the predicted value (e.g., in the indicated units). The microprocessor then employs an algorithm to compare the predicted value to the threshold value(s). If the predicted value falls above a high threshold, below a low threshold, or outside of a predetermined range of values, then the microprocessor triggers the analyte monitoring system to provide an alert to the user.

When the analyte being monitored is glucose and glucose readings are provided by a glucose monitoring device (e.g., the GlucoWatch biographer) $y_n$ corresponds to $GW_n$, a glucose value in the subject at time $t_n$. Further, for prediction of glucose values when using Eqn. 11, $\alpha$ typically equals 0.5.

Eqn. 11 predicts the next analyte value ($y_{(n+1)}$) based on the current analyte value ($y_n$), and two previous analyte values $y_{(n-1)}$ and $y_{(n-2)}$, wherein the weight of the effect of $y_{(n-2)}$ is determined by the weighting factor α. Eqn. 12 predicts the next analyte value ($y_{(n+1)}$) based on the current analyte value ($y_n$), a previous analyte value $y_{(n-1)}$, and time intervals associated with the times at which the analyte values are determined (for ($y_n$) and $y_{(n-1)}$) or predicted ($y_{(n-1)}$). Eqn. 13 predicts the next analyte value ($y_{(n+1)}$) based on the current analyte value ($y_n$), and two previous analyte values $y_{(n-1)}$ and $y_{(n-2)}$. Eqn. 14 predicts an analyte value($y_{(n+2)}$) at two time points after $t_n$ based on the current analyte value ($y_n$), a previous analyte value $y_{(n-2)}$, and time intervals associated with the times at which the analyte values are determined (for ($y_n$) and $y_{(n-2)}$) or predicted ($y_{(n+2)}$). Eqn. 15 predicts an analyte value($y_{(n+2)}$) at two time points after $t_n$ based on the current analyte value ($y_n$), a previous analyte value $y_{(n-1)}$), and time intervals associated with the times at which the analyte values are determined (for ($y_n$) and $y_{(n-1)}$) and predicted ($y_{(n+2)}$).

As noted above, when employing the above predictive algorithms, an alert/alarm can be used to notify the subject (or user) if the predicted value is above/below a predetermined threshold. For example, in the situation where glucose is the analyte being monitored, a low threshold of greater than 80 mg/dL may be selected for a particular subject. Accordingly predicted glucose values (obtained by using any of the above predictive algorithms) of 80 or less may trigger an alert to the subject. Typically low threshold values for glucose are between about 50–100 mg glucose per dL blood and high threshold values are between about 200–300 mg glucose per dL blood.

C. Combined Approach

In one embodiment of the present invention to provide an analyte concentration-related alert when an analyte level falls above or below predetermined thresholds or outside of a predetermined range of reference values, an approach combining the above-described gradient method and predictive algorithm method is employed. In this embodiment of the present invention, rate of change thresholds are determined as well as analyte thresholds (or range of values). Generally, a predictive algorithm is chosen which provides a predicted analyte value at a future time point. The predicted value is compared to the threshold value for the alert. If the predicted value exceeds the threshold value, then the rate of change of the analyte is evaluated. If the rate of change of the analyte level surpasses a predetermined threshold (or falls outside of a range of values) then an analyte concentration-related alert is provided to the subject in whom the analyte levels are being monitored. Of course the order of these two comparisons (i.e., predicted value and rate of change) may be reversed, for example, where the rate of change is evaluated first and then the predicted value is evaluated.

For example, in the context of providing an alert for a future hypoglycemic event, a "low alert threshold" is selected. Such a threshold is typically user selected and falls in the range of about 50 mg/dL (glucose/blood volume) to about 100 mg/dL. Additionally, one or more microprocessors of the monitoring system may be programmed to modify the user the selected threshold by, for example, adding a predetermined value to the selected threshold (for example, if a threshold of 80 mg/dL is selected a program of the monitoring system may add 10 mg/dL to the threshold, resulting in a low alert threshold of 90 mg/dL).

A predictive algorithm is chosen (e.g., based on Eqn. 15, above)

$$GW_{(n+2)} = GW_{(n)} + \frac{(GW_{(n)} - GW_{(n-1)})}{(t_n - t_{(n-1)})} * (t_{(n+2)} - t_n)). \quad \text{Eqn. 16}$$

When the current glucose value, e.g., as determined by the GlucoWatch biographer, is equal to or less than a predetermined value the predictive algorithm is invoked to predict a glucose value at a future time point (for Eqn. 16 that would be n+2). Simultaneously, or sequentially, a gradient method is employed to determine the rate of change of the glucose values, for example, using Model B above where y equals the glucose value as determined by the GlucoWatch biographer, and the threshold fractional change/time (e.g., %/min) is defined, for example, as negative 5%/10 minutes:

$$\text{Model B}' \quad \frac{GW_{(n)} - GW_{(n-1)}}{GW_{(n-1)}\Delta t}.$$

The rate of change as determined by the gradient method is compared to a threshold value or range of threshold values. If the glucose value predicted by the predictive algorithm is less than or equal to the predetermined low threshold value, and the rate of change is negative and less than the predetermined threshold rate of change then an alert is provided to the subject in anticipation of a hypoglycemic event.

The present invention includes, but is not limited to, methods, microprocessors programmed to execute the methods, and monitoring systems (comprising, for example, a sampling device, a sensing device, and one or more microprocessors programmed to control, for example, (i) a measurement cycle utilizing the sampling and sensing devices, and (ii) data gathering and data processing related to the methods of the present invention).

In one aspect of the present invention, one or more microprocessors employ an algorithm comprising programmed instructions to execute the above described combined methods for providing an analyte-concentration related alert. Typically, such one or more microprocessors are components of an analyte monitoring system.

In one aspect of the present invention, the rolling values described above are employed as the measurement data points in the "analyte concentration-related" alert methods. As noted above, the rolling value method of the present invention provides for more frequent updating and reporting of analyte measurement values. In a further aspect of the present invention interpolation and/or extrapolation methods are employed to provide missing or error-associated signals in the series of analyte-related signals. As discussed above, one or more microprocessors may be programmed to execute the calculations associated with a rolling value method and/or an analyte-concentration related alert method.

As is apparent to one of skill in the art, various modification and variations of the above embodiments can be made without departing from the spirit and scope of this invention. Such modifications and variations are within the scope of this invention.

What is claimed is:

1. A method of increasing the number of analyte measurement values related to the amount or concentration of an analyte in a subject as measured using an analyte monitoring device, said method comprising providing a series of analyte-related signals obtained from the analyte monitoring device over time, wherein (a) two or more contiguous analyte-related signals are used to obtain a single analyte measurement value (M), (b) analyte-related signals are not used to calculate more than one analyte measurement value, and (c) said two or more contiguous analyte-related signals, used to obtain the single analyte measurement value, comprise first and last analyte-related signals of the series;

mathematically computing rolling analyte measurement values, wherein (i) each rolling analyte measurement value is calculated based on two or more contiguous analyte-related signals from the series of analyte-related signals obtained from the analyte monitoring device, (ii) a subsequent rolling analyte measurement value is mathematically computed by dropping said first analyte-related signal and including an analyte-related signal contiguous and subsequent to the last analyte-related signal, (iii) further rolling analyte measurement values are obtained by repeating the dropping of the first analyte-related signal used to calculate the previous rolling analyte measurement and including an analyte-related signal contiguous and subsequent to the last analyte-related signal used to calculate the previous rolling analyte measurement, and (iv) each rolling analyte measurement value provides a measurement related to the amount or concentration of analyte in the subject; and increasing the number of analyte measurement values derived from the analyte-related signals in the series of analyte-related signals obtained from the analyte monitoring device by serially calculating rolling analyte measurement values, thereby increasing the number of analyte measurement values relative to the number of analyte measurement values provided when two or more contiguous analyte-related signals are used to obtain a single analyte measurement value (M) and analyte-related signals are not used to calculate more than one analyte measurement value.

2. The method of claim 1, wherein said rolling analyte measurement value is an average of two or more analyte-related signals.

3. The method of claim 1, wherein said rolling analyte measurement value is a sum of two or more analyte-related signals.

4. The method of claim 1, wherein each analyte-related signal is represented by an integral over time, and said rolling analyte measurement value is obtained by integral splitting.

5. The method of claim 1, wherein said monitoring device comprises a sampling device and a sensing device, and wherein said providing the series of analyte-related signals obtained from an analyte monitoring device comprises extracting a sample from the subject alternately into a first collection reservoir and then into a second collection reservoir using the sampling device, wherein (i) each sample comprises the analyte, and (ii) said sampling device comprises said first and second collection reservoirs; and sensing the analyte in each extracted sample to obtain a signal from each sample that is related to the analyte amount or concentration in the subject, thus providing a series of analyte-related signals, said sensing device comprising first and second sensors, wherein said first sensor is in operative contact with said first collection reservoir and said sensing provides signal $S^A_j$ (where $S_A$ is the signal from sensor A, j is the time interval), the second sensor is in operative contact with the second collection reservoir and said sensing provides signal $S^B_{j+1}$ (where $S^B$ is the signal from sensor B, j+1 is the time interval), and an analyte measurement value is obtained using analyte-related signal from sensor A and sensor B.

6. The method of claim 5, wherein said rolling analyte measurement values are calculated as follows:

$$(\text{average signal})_j = (S^B_{j-1} + S^A_j)/2; \qquad \text{Eqn. 1}$$

$$(\text{average signal})_{j+1} = (S^A_j + S^B_{j+1})2; \qquad \text{Eqn. 2}$$

$$(\text{average signal})_{j+2} = (S^B_{j+1} + S^A_{j+2})/2; \text{ etc.}, \qquad \text{Eqn. 3}$$

wherein (i) (j−1) is the measurement half-cycle previous to j, and (j+2) is two measurement half-cycles after j; and (ii) each average signal corresponds to a rolling analyte measurement value.

7. The method of claim 5, wherein said rolling analyte measurement values are calculated as follows:

$$(\text{summed signal})_j = (S^B_{j-1} + S^A_j); \qquad \text{Eqn. 4}$$

$$(\text{summed signal})_{j+1} = (S^A_j + S^B_{j+1}); \text{ and} \qquad \text{Eqn. 5}$$

$$(\text{summed signal})_{j+2} = (S^B_{j+1} + S^A_{j+2}); \text{ etc.} \qquad \text{Eqn. 6}$$

where (j−1) is the measurement half-cycle previous to j, and (j+2) is two measurement half-cycles after j; and (ii) each summed signal corresponds to a rolling analyte measurement value.

8. The method of claim 1, wherein a missing or error-associated signal in the series of analyte-related signals obtained from the analyte monitoring device is estimated using interpolation before mathematically computing rolling analyte measurement values.

9. The method of claim 1, wherein a missing or error-associated signal in the series of analyte-related signals obtained from the analyte monitoring device is estimated using extrapolation before mathematically computing rolling analyte measurement values.

10. The method of claim 1, wherein said analyte is glucose.

11. The method of claim 1, wherein said analyte monitoring device comprises at least one sensing device.

12. The method of claim 1, wherein said analyte-related signal is a current or a charge related to amount or concentration of analyte in the subject.

13. The method of claim 1, wherein one or more microprocessors comprise programming to control mathematical computation of rolling analyte measurement values.

14. The method of claim 13, wherein said one or more microprocessors comprise programming to control at least one component of the analyte monitoring device.

15. The method of claim 14, wherein said analyte monitoring device comprises at least one sampling device and at least one sensing device.

16. The method of claim 15, wherein said one or more microprocessors control obtaining samples from the subject and sensing analyte concentration in each obtained sample to provide the series of analyte-related signals.

17. The method of claim 16, wherein said analyte monitoring device comprises (i) an iontophoretic sampling device, and (ii) an electrochemical sensing device.

18. The method of claim 11, wherein said sensing device comprises a biosensor device.

19. The method of claim 18, wherein said biosensor device comprises an electrode used in electrochemical detection of analyte.

20. The method of claim 11, wherein said analyte monitoring device further comprises at least one sampling device.

21. The method of claim 20, wherein said sampling device employs a sampling method selected from the group consisting of iontophoresis, sonophoresis, microdialysis, suction, and passive diffusion.

22. One or more microprocessors comprising programming to:
  control mathematical computation of rolling analyte measurement values, wherein (i) each rolling analyte measurement value is calculated based on two or more contiguous analyte-related signals from a series of analyte-related signals obtained from an analyte monitoring device, (ii) said series of analyte-related signals is obtained from the analyte monitoring device over time, wherein (a) two or more contiguous analyte-related signals are used to obtain a single analyte measurement value (M), (b) analyte-related signals are not used to calculate more than one analyte measurement value, and (c) said two or more contiguous analyte-related signals, used to obtain the single analyte measurement value, comprise first and last analyte-related signals of the series, (iii) a subsequent rolling analyte measurement value is mathematically computed by dropping said first analyte-related signal and including an analyte-related signal contiguous and subsequent to the last analyte-related signal, (iv) further rolling analyte measurement values are obtained by repeating the dropping of the first analyte-related signal used to calculate the previous rolling analyte measurement and including an analyte-related signal contiguous and subsequent to the last analyte-related signal used to calculate the previous rolling analyte measurement, and (v) each rolling analyte measurement value provides a measurement related to the amount or concentration of analyte in the subject; and
  increase the number of analyte measurement values derived from the analyte-related signals in the series of analyte-related signals obtained from the analyte monitoring device by serially calculating rolling analyte measurement values, thereby increasing the number of analyte measurement values relative to the number of analyte measurement values provided when two or more contiguous analyte-related signals are used to obtain a single analyte measurement value (M) and analyte-related signals are not used to calculate more than one analyte measurement value.

23. The one or more microprocessors of claim 22, wherein said analyte monitoring device comprises at least one sensing device and said one or more microprocessors are further programmed to control operation of said sensing device.

24. The one or more microprocessors of claim 23, wherein said analyte monitoring device further comprises at least one sampling device and said one or more microprocessors are further programmed to control operation of said sampling device.

25. The one or more microprocessors of claim 24, wherein said one or more microprocessors control obtaining samples from the subject and sensing analyte concentration in each obtained sample to provide the series of analyte-related signals.

26. The one or more microprocessors of claim 22, wherein said rolling analyte measurement value is an average of two or more analyte-related signals.

27. The one or more microprocessors of claim 22, wherein said rolling analyte measurement value is a sum of two or more analyte-related signals.

28. The one or more microprocessors of claim 22, wherein each analyte-related signal is represented by an integral over time, and said rolling analyte measurement value is obtained by integral splitting.

29. The one or more microprocessors of claim 22, wherein said monitoring device comprises a sampling device and a sensing device, and wherein said providing the series of analyte-related signals obtained from an analyte monitoring device comprises
  extracting a sample from the subject alternately into a first collection reservoir and then into a second collection reservoir using the sampling device, wherein (i) each sample comprises the analyte, and (ii) said sampling device comprises said first and second collection reservoirs; and
  sensing the analyte in each extracted sample to obtain a signal from each sample that is related to the analyte amount or concentration in the subject, thus providing a series of analyte-related signals, said sensing device comprising first and second sensors, wherein said first sensor is in operative contact with said first collection reservoir and said sensing provides signal $S^A_j$ (where $S^A$ is the signal from sensor A, j is the time interval), the second sensor is in operative contact with the second collection reservoir and said sensing provides signal $S^B_{j+1}$ (where $S^B$ is the signal from sensor B, j+1 is the time interval), and an analyte measurement value is obtained using analyte-related signal from sensor A and sensor B.

30. The one or more microprocessors of claim 29, wherein said rolling analyte measurement values are calculated as follows:

$$(\text{average signal})_j = (S^B_{j-1} + S^A_j)/2; \qquad \text{Eqn. 1}$$

$$(\text{average signal})_{j+1} = (S^A_j + S^B_{j+1})/2; \qquad \text{Eqn. 2}$$

$$(\text{average signal})_{j+2} = (S^B_{j+1} + S^A_{j+2})/2; \text{ etc.,} \qquad \text{Eqn. 3}$$

wherein (i) (j−1) is the measurement half-cycle previous to j, and (j+2) is two measurement half-cycles after j, and (ii) each average signal corresponds to a rolling analyte measurement value.

31. The one or more microprocessors of claim 29, wherein said rolling analyte measurement values are calculated as follows:

$$(\text{summed signal})_j = (S^B_{j-1} + S^A_j); \qquad \text{Eqn. 4}$$

$$(\text{summed signal})_{j+1} = (S^A_j + S^B_{j+1}); \text{ and} \qquad \text{Eqn. 5}$$

$$(\text{summed signal})_{j+2} = (S^B_{j+1} + S^A_{j+2}); \text{ etc.} \qquad \text{Eqn. 6}$$

where (j−1) is the measurement half-cycle previous to j, and (j+2) is two measurement half-cycles after j; and (ii) each summed signal corresponds to a rolling analyte measurement value.

32. The one or more microprocessors of claim 22, wherein a missing or error-associated signal in the series of analyte-related signals obtained from the analyte monitoring device is estimated using interpolation before mathematically computing rolling analyte measurement values.

33. The one or more microprocessors of claim 22, wherein a missing or error-associated signal in the series of analyte-related signals obtained from the analyte monitoring device is estimated using extrapolation before mathematically computing rolling analyte measurement values.

34. The one or more microprocessors of claim 22, wherein said analyte is glucose.

35. The one or more microprocessors of claim 34, wherein said analyte monitoring device comprises (i) an iontophoretic sampling device, and (ii) an electrochemical sensing device.

36. The one or more microprocessors of claim 22, wherein said analyte-related signal is a current or a charge related to amount or concentration of analyte in the subject.

37. An analyte monitoring device comprising:
a sensing device; and
one or more microprocessor programmed to control operation of said sensing device, and
control mathematical computations of rolling analyte measurement values, wherein (i) each rolling analyte measurement value is calculated based on two or more contiguous analyte-related signals from a series of analyte-related signals obtained from an analyte monitoring device, (ii) said series of analyte-related signals is obtained from the analyte monitoring device over time, wherein (a) two or more contiguous analyte-related signals are used to obtain a single analyte measurement value (M), (b) analyte-related signals are not used to calculate more than one analyte measurement value, and (c) said two or more contiguous analyte-related signals, used to obtain the single analyte measurement value, comprise first and last analyte-related signals of the series, (iii) a subsequent rolling analyte measurement value is mathematically computed by dropping said first analyte-related signal and including an analyte-related signal contiguous and subsequent to the last analyte-related signal, (iv) further rolling analyte measurement values are obtained by repeating the dropping of the first analyte-related signal used to calculate the previous rolling analyte measurement and including an analyte-related signal contiguous and subsequent to the last analyte-related signal used to calculate the previous rolling analyte measurement, and (v) each rolling analyte measurement value provides a measurement related to the amount or concentration of analyte in the subject increasing the number of analyte measurement values derived from the analyte-related signals in the series of analyte-related signals obtained from the analyte monitoring device by serially calculating rolling analyte measurement values, thereby increasing the number of analyte measurement values relative to the number of analyte measurement values provided when two or more contiguous analyte-related signals are used to obtain a single analyte measurement value (M) and analyte-related signals are not used to calculate more than one analyte measurement value.

38. The analyte monitoring device of claim 37, wherein said analyte monitoring device further comprises a sampling device.

39. The analyte monitoring device of claim 38, wherein said one or more microprocessors are further programmed to control the operation of said sampling device.

40. The analyte monitoring device of claim 38, wherein said sampling device employs a sampling method selected from the group consisting of iontophoresis, sonophoresis, microdialysis, suction, and passive diffusion.

41. The analyte monitoring device of claim 39, wherein said analyte monitoring device comprises (i) an iontophoretic sampling device, and (ii) an electrochemical sensing device.

42. The analyte monitoring device of claim 37, wherein said sensing device comprise a biosensor device.

43. The analyte monitoring device of claim 42, wherein said biosensor device comprises an electrode used in electrochemical detection of analyte.

* * * * *

UNITED STATES PATENT AND TRADEMARK OFFICE
CERTIFICATE OF CORRECTION

PATENT NO. : 7,011,630 B2 Page 1 of 1
APPLICATION NO. : 10/176965
DATED : March 14, 2006
INVENTOR(S) : Shashi P. Desai et al.

It is certified that error appears in the above-identified patent and that said Letters Patent is hereby corrected as shown below:

Column 49, claim 5, line 67, delete $S_A$, and insert -- $S^A$ --.

Column 50, claim 6, line 11, please add after $(S^A{}_j{}^+ S^B{}_{j+1})$ --/--.

Signed and Sealed this

Twenty-second Day of August, 2006

JON W. DUDAS
*Director of the United States Patent and Trademark Office*